United States Patent
McGovern et al.

[11] Patent Number: 6,159,695
[45] Date of Patent: Dec. 12, 2000

[54] HIGH SURFACE DENSITY COVALENT IMMOBILIZATION OF OLIGONUCLEOTIDE MONOLAYERS

[76] Inventors: Mark McGovern, 25 Clearside Place, Etobicoke, Canada, M9R 2G7; Michael Thompson, 170 College Street, Toronto, Canada, M5S 3E3

[21] Appl. No.: 09/301,287

[22] Filed: Apr. 28, 1999

Related U.S. Application Data

[63] Continuation-in-part of application No. 08/951,448, Oct. 16, 1997.
[51] Int. Cl.[7] .............................. C12Q 1/68; C12P 19/34; B05D 3/00
[52] U.S. Cl. .................................. 435/6; 435/6; 435/91.2; 427/299
[58] Field of Search ........................ 435/6, 91.2; 427/299

[56] References Cited

PUBLICATIONS

Li et al., "Synthesis, characterization, and properties of covalently bound, self–assembled porphyrin multilayer thin films" Chem. Mater. vol. 6, pp. 803–810, 1994.

Chrisey, et al., "Covalent attachment of synthetic DNA to self–assembled monolayer films", Nucleic Acids Research, 1996, vol. 24, No. 15, 3031–3039.

Wasserman et al., "Structure and reactivity of alkylsiloxane monolayers formed by reaction of alkyltrichlorosilanes on silicon substrates", Langmuir 1989, 5, 1074–1087.

Yee et al., "Modification of quartz surfaces via thiol–disulfide interchange", Langmuir, vol. 7, No. 2, 1991, 308–313.

Carlsson et al., "Immobilization of urease by thiol–disulphide interchange with concimitant purification", Eur. J. Biochem. 44, 189–194 (1974).

(List continued on next page.)

*Primary Examiner*—John S. Brusca
*Assistant Examiner*—Jeffrey S Lundgren
*Attorney, Agent, or Firm*—Ridout & Maybee

[57] ABSTRACT

Oligonucleotides and other biomolecules are immobilized in high density on solid substrates through covalent forces using either a permanent thioether bond, or a chemoselectively reversible disulfide bond to a surface thiol. Substrates which have hydroxyl groups on their surfaces can be first silanized with a trichlorosilane containing 2–20 carbon atoms in its hydrocarbon backbone, terminating in a protected thiol group. The oligonucleotides or other biomolecules are first connected to a tether consisting of a hydrocarbon or polyether chain of 2–20 units in length which terminates in a thiol group. This thiol may be further modified with a halobenzylic-bifunctional water soluble reagent which allows the conjugate to be immobilized onto the surface thiol group by a permanent thioether bond. Alternatively, the oligonucleotide-tether-thiol group can be converted to a pyridyldisulfide functionality which attaches to the surface thiol by a chemoselectively reversible disulfide bond. The permanently bound oligonucleotides are immobilized in high density compared to other types of thiol functionalized silane surface and to the avidin-biotin method.

9 Claims, 5 Drawing Sheets

OTHER PUBLICATIONS

Wirth et al., "Influence of ligand density on the properties of metal–chelate affinity supports", Analytical Biochemistry 208, 16–25 (1993).

Mandenius et al., "The interaction of proteins and cells with affinity ligands covalently coupled to silicon surfaces as monitored by ellipsometry", Analytical Biochemistry 137, 106–114 (1984).

Kallury et al., Enhancement of the thermal and storage stability of urease by covalent attachment to phospholipid–ound silica, Anal. Chm. 1992, 64, 1062–1068.

Hong et al., "Cysteine–specific surface tethering of genetically engineered cytochromes for fabrication of metalloprotein nanostructures", Langmuir 1994, 10, 153–158.

Lu et al., "The binding of bifunctional reagents to silanized silicon surfaces studies by angle–dependent X–ray photoelectron spectroscopy", Applied Surface Science 72 (1993) 125–132.

Maskos et al., "Oligonucleotide hybridisations on glass supports: a novel linker for oligonucleotide synthesis and hybridisation properties of oligonucleotides synthesised in situ", Nucleic Acids Research, vol. 20, No. 7, 1679–1684.

Maitra et al., "Silanization of DNA bound baked glass permits enhanced polymerization by Dna polymerase", Current Science, vol. 62, No. 8, 586–588.

Ghosh et al., "Covalent attachment of oligonucleotides to solid supports", Nucleic Acids Research, vol. 15, No. 13, 1987, 5353–5363.

A) Silanization of Substrate With TTU

1 % TTU (6), 100-x % octyltrichlorosilane (14)
$\longrightarrow$
1 mM in dry toluene, 2h, r.t.

B) Deprotection After Silanization 0.5 M Hydroxylamine
pH = 8.5, 2h, r.t.

Oligonucleotide-tether-linker coupling schemes

A) Attachment of Thiol tether to Oligonucleotide

Oligonucleotide + tether-SH  ⎯→  Oligonucleotide - tether-SH
    17       18                                            19

18 a) column
        18 b) phosphoramidite
        18 c) enzymatic coupling

B) Coupling of BMBS to Oligonucleotide-Thiol Tether Complex

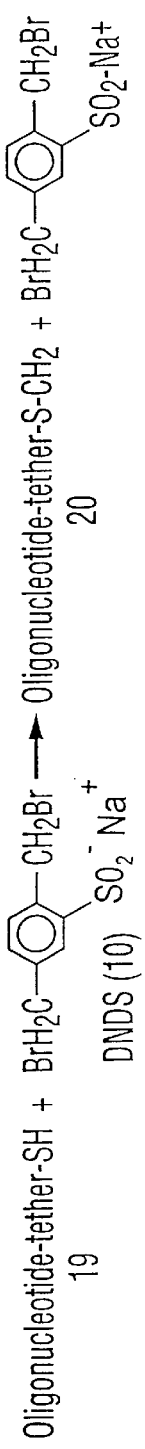

Oligonucleotide-tether-SH  +  BrH$_2$C—⟨phenyl⟩—CH$_2$Br  ⎯→  Oligonucleotide-tether-S-CH$_2$—⟨phenyl⟩—CH$_2$Br  +  BrH$_2$C—⟨phenyl⟩—CH$_2$Br
    19                      DNDS (10)  SO$_2^-$ Na$^+$                                  20                          SO$_2^-$ Na$^+$ C) Addition of Pyridyldisulfide Group to Oligonucleotide-Thiol Tether Complex Via DNDS

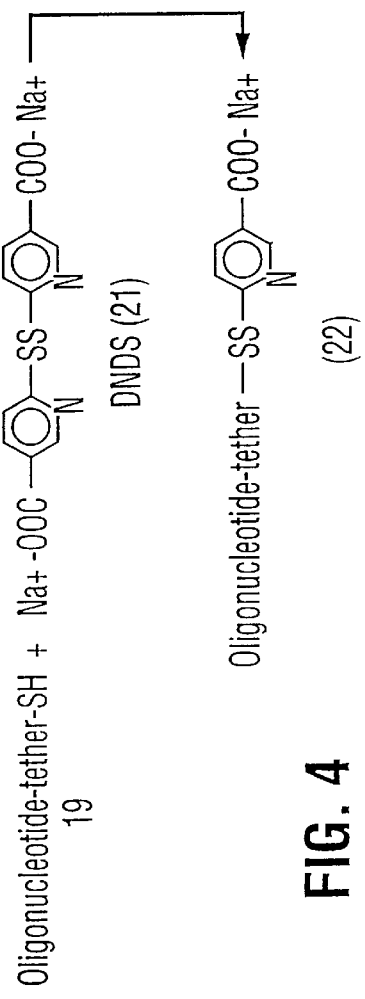

Oligonucleotide-tether-SH  +  Na$^+$ $^-$OOC—⟨pyridyl⟩—SS—⟨pyridyl⟩—COO$^-$ Na$^+$
    19                                DNDS (21)

Oligonucleotide-tether—SS—⟨pyridyl⟩—COO$^-$ Na$^+$
(22)

FIG. 4

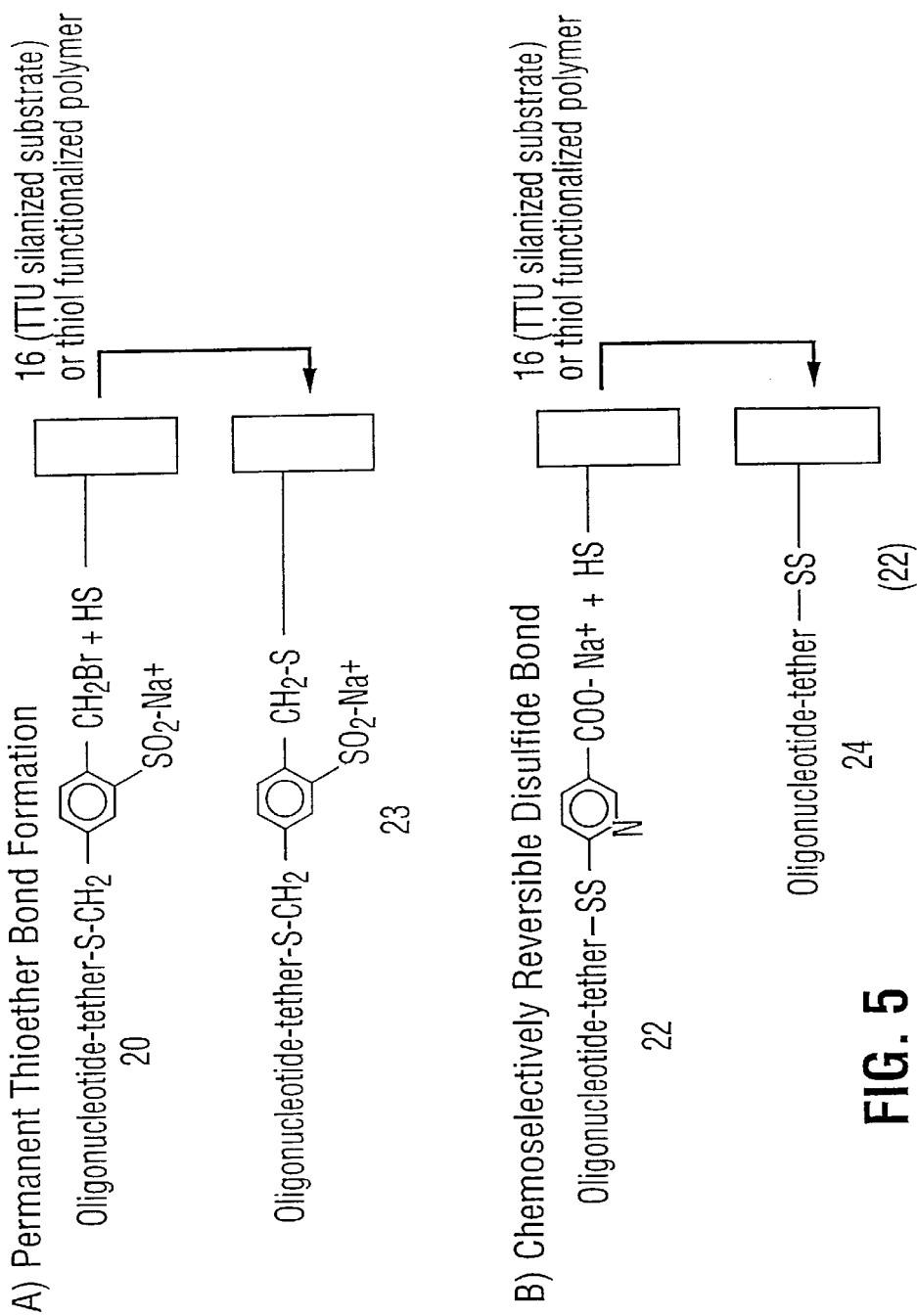

HIGH SURFACE DENSITY COVALENT IMMOBILIZATION OF OLIGONUCLEOTIDE MONOLAYERS

CROSS-REFERENCE TO RELATED APPLICATIONS

This application is a continuation-in-part of U.S. patent application Ser. No. 08/954,448 filed Oct. 16, 1997, the entire disclosure of which is incorporated herein by reference.

FIELD OF THE INVENTION

This invention relates biochemical sensor element structures of the type in which covalently immobilized biomolecules such as nucleic acids are covalently bound onto solid supports, and to methods for their preparation. More particularly, it provides such structures in which a trichlorosilane adhesion agent forms a monolayer film and provides a reactive functionality to which oligonucleotides and other biomolecules such as enzymes can be attached in very high density. Included in the invention are processes for the synthesis of the silane, synthesis of novel bifunctional linkers for nucleic acid modification, and immobilization protocols.

BACKGROUND OF THE INVENTION AND PRIOR ART

Medical diagnosis and treatment of diseases at the genetic level is quickly becoming a reality. Drug design strategies will increasingly depend on developing new methods for regulating gene expression. Early detection of infectious viral diseases and genetic mutations using fast, reliable diagnostic techniques combined with gene-therapy strategies create the possibility of effecting a cure before symptoms of the disease appear. New technologies based on gene isolation and purification, synthesis, amplification, and detection are required to meet these challenges. These emerging technologies require improved methods for oligonucleotide immobilization in several key fields including: nucleic acid separation/purification; nucleic acid amplification (solid-phase PCR); oligonucleotide synthesis; isolation of nucleic acid binding proteins and drugs; detection of oligonucleotides through hybridization; and sequencing.

Amplification of Oligonucleotides by Solid Phase PCR

The polymerase chain reaction (PCR) is a rapid procedure for producing many copies of a specific segment of DNA in vitro. This technique has now made possible many applications such as molecular genetic research, gene sequencing, forensic/criminal and clinical investigations and many others in which only a minuscule quantity of DNA is available. PCR was originally developed for the solution phase and requires four essential ingredients; Taq DNA polymerase which is the enzyme responsible for building the new DNA copies, the original DNA strand to be amplified, the four triphosphate bases, and finally, the priming sequences from which the new DNA copies will grow. A much improved method is to attach the priming sequences to a solid support which allows the amplified DNA to be chemoselectively removed after the reaction is completed.

Oligonucleotide Synthesis Via Solid Phase Methods

Short fragments of single-stranded DNA or RNA of any desired sequence can be rapidly synthesized using an automated DNA synthesizer which is now commonplace in many laboratories. Oligonucleotides are made by the sequential addition of activated monomers to a growing chain that is linked to an insoluble solid support. The solid-phase synthetic method has the following advantages: reaction yields can be near-quantitative by using excess reagents which can then be easily removed by filtration processes; the repetitive synthesis is readily automated; handling is minimized thereby decreasing the risk of contamination; and wastage of expensive reagents is also minimized. Functionalized polystyrene beads or carboxyl-derivatized controlled-pore-glass are commonly used as supports, with the powdered material being sealed into a tube which has porous frits at both ends. Usually, the first nucleotide is attached to the solid support via a carboxylic ester link to the 3' hydroxyl, and synthesis is carried out in the 3'–5' direction. A high ratio of oligonucleotide to surface area is required to optimally perform the synthesis to prevent wasteage of reagents. It is advantageous to attach special tethering groups to one of the chain ends to act as a chemical "handle" so that the single-stranded nucleic acid can be attached to other solid surfaces such as affinity columns or biosensor devices. Solid phase synthesis and the immobilization technology to which it is dependent, can be applied to the synthesis of other types of biopolymers including peptides, proteins, and combinatorial synthesis of diverse arrays of any class of molecule.

Separation, Isolation and Purification of Oligonucleic Acids, Oligonucleotide-Other Molecule Complexes and Other Biomolecules Biomolecules in general can be purified by electrophoretic, chromatographic, filtration or by affinity techniques. Electrophoresis is widely used to separate nucleic acid fragments in a gel matrix. The fragments are usually transferred or "blotted" onto a membrane which has an affinity for the nucleic acids so that further processing can be accomplished. Reverse-Phase Liquid Chromatography (RPLC) has been used to separate mixtures of nucleic acids, proteins and other biomolecules on coated solid supports. Microfiltration is used to remove impurities from biomolecule preparations.

Improved separations can be achieved by immobilizing various sequences of nucleic acids onto the stationary media to produce an "affinity" hybrid technique. Single-stranded nucleic acids can be immobilized onto a solid support, to which the complementary strand can specifically hybridize; such a technique is referred to as hybridization. Impurities are washed away, while the complementary strand remains affixed, and elution selectively occurs when variables such as buffer strength are changed. In such a manner, improved electrophoresis membranes for "Northern blots", nucleic acid chromatographic supports, and nucleic acid binding filtration media can be made.

Molecules other than nucleic acids can specifically recognize immobilized nucleic acids. Research to discover new treatments for genetic diseases requires the development of novel methods for investigating the interactions of genes with regulatory proteins. Gene transcription, replication and repair are mediated by many DNA or RNA binding proteins. Drugs such as cis-diaminedichloroplatinum (II) known as "cisplatin" which has antitumor activity for the treatment of ovarian, bladder and testicular cancer, anthracycline antibiotics and polycyclic aromatic compounds can intercalate into DNA structures. Antisense drug therapy innovations are directed at strongly binding a complementary segment of nucleic acid material to the target gene in a highly selective fashion. Similar to nucleic acid purification through immobilized hybridization as mentioned earlier, proteins, drugs and any type of nucleic acid binding molecule can be purified through selective interactions with immobilized oligonucleotides. In all cases, a high density of immobilized oligonucleotides will result in increased efficiency, together with minimization of waste production.

Detection of Oligonucleotides, Antisense Compounds and Small Molecules

Detection of oligonucleotides for diagnostic assays through hybridization and sequencing is also dependant on high density surface immobilization of oligonucleotides. Determining genetic sequences is a well established field. Standard techniques such as electrophoretic separation of partially digested nucleic acid fragments are generally too slow for clinical work. A different approach is sequencing by hybridization or SBH in which a library of short oligonucleotide probes, labelled in some way, and of known sequence, are presented to unknown DNA. When complementary sequences are found, a process known as hybridization occurs which allows for signalling the presence of a particular sequence in the gene. New techniques such as micromachined capillary electrophoresis arrays require high density immobilization techniques, as each channel possesses a very minute surface area.

Immobilized nucleic acid probes on sensor surfaces can provide much faster analyses at a fraction of the cost. Such is the basis for a "gene chip" in which vast arrays of different genetic probes, approximately 10–30 bases in length are immobilized onto a silicon wafer similar to those used in computer chip manufacture. The parallel revolution in microelectronics, combined with advances in automated nucleic acid synthesis has generated the development of new biosensor devices for the analysis of gene sequences and drug discovery schemes. A biosensor is a device which transforms biological information into electronic form which can then be readily interfaced with computer technology. Most biosensors include a biochemical sensor element structure comprising a platform, usually a solid surface, to which the biologically active probe molecules are attached. Biomolecules such as DNA are extremely selective, and can efficiently bind to a specific target molecule in a solution containing many other species. The probe-target interaction is then observed by a mechanism (optical, electrochemical or piezoelectric) which can transduce chemical information to electronic data. All of these techniques can deliver information in real-time, which is a benefit that the standard techniques do not possess.

The nucleic acid probe should be immobilized to the surface in some way so that the biosensor can be continuously reused in a flow injection analysis (FIA) format. The nucleic acid probes must be immobilized in the correct concentration, under mild conditions, rapidly, among many other considerations. The biosensor surface can be tailored so that more than one type of nucleic acid is attached to its surface. The use of photoprotective schemes has been reported as being capable of producing patterned surfaces.

Immobilization Methodology

Numerous techniques have been developed for the immobilization of enzymes and antibodies (Mosbach (ed.), Methods in Enzymology, Vol. 137, 1988) and many of the techniques used to immobilize proteins can also be adapted for nucleic acids (Dunlap, Advances in Experimental Medicine and Biology). Adsorption is the simplest method to attach nucleic acids to surfaces, since no reagents or special nucleic modifications are required. Non-covalent forces affix the nucleic acid to such materials as nitrocellulose, nylon membranes (Brent et. al., Current Protocols in Molecular Biology, 1993) polystyrene or metal oxide surfaces such as palladium or aluminum oxide. The main disadvantages of these methods are that the nucleic acid may be readily desorbed from the substrate by hybridization conditions, and the base moieties may be unavailable for hybridization if they are bonded to the substrate. Crosslinking or entrapment (Licache et. al., Nucleic Acids Res., 1994, 22, 2915) in polymeric films has been used to create a more permanent nucleic acid surface. The nucleic acid can be crosslinked by exposure to U.V. light (pyrimidine-pyrimidine dimer). Vinyl-substituted nucleotides have been made which can polymerize (Pitha, Polymer, 1977, 18, 425). The nucleic acid can be embedded in an amino-containing dextran matrix (Johnsson et. al., Anal. Biochem., 1991, 198, 268) or aminoethylcellulose crosslinked with gluteraldehyde, silica, or in polyacrylamide.

Avidin/streptavidin-biotin complexation has found considerable application in the nucleic acid biosensor field (Ebersole et. al., J. of the Amer. Chem .Soc., 1990, 112, 3239). Avidin and streptavidin are large proteins (70 kD) which each contain 4 biotin binding sites. Biotin is a small molecule which attaches with very high affinity to the binding site ($K_d=10^{-15}$ M), and can only be removed under the most extreme conditions. The avidin is first adsorbed onto the substrate, and is then exposed to an aqueous solution of biotinylated nucleic acid. The inherent aqueous stability of avidin and biotin makes the system easy to handle. However, the presence of the large protein layer may present non-specific binding sites and compromise the sensitivity and selectivity of certain types of sensors.

Alternatively, the nucleic acid can be constructed with a thiol linker which can be used to directly complex to gold surfaces (Ito, et. al., Anal. Chim. Acta., 1996, 327, 29). It is desirable to fashion assemblies similar to the long-chain self-assembled monolayers of alkanethiols which have been described in the literature (Van Ness et. al., Nucleic Acids Res., 1991, 19, 3345). The thiol-nucleic acid probably cannot produce a close-packed surface due to the large hydrophilic nucleic acid group, and therefore its stability is questionable.

It is desirable to attach the nucleic acid covalently to a surface of the support by a linker attached to one of the ends of the nucleic acid chain. By doing so, the nucleic acid probe is free to change its conformation so that hybridization can take place, yet cannot be displaced from the sensor. Much work has centered in this area, with early attempts being based on attaching the 3' hydroxyl or phosphate group to carboxyl residues on various celluloses using carbodiimide derivatives (Schott, Affinity Chromatography: Template Chromatography of Nucleic Acids and Proteins, 1984). Cyanuric chloride (Biagione et. al., Anal. Biochem., 1978, 89, 616) has been used to react oligonucleotides to a variety of materials. Cyanogen bromide (Scowten, Affinity Chromatography: Bioselective Adsorption of Inert Matrices, 1986) has been used to link one or more exocyclic amine residues to agarose via isourea ether groups. Carboxylic acid and aldehyde modified nucleic acids have been attached to latex spheres via hydrazide or Schiff-base type linkages (Kremsky et. al., Nucleic Acids Res., 1987, 15, 2891).

Many biosensor surfaces consist of silica or metal oxide. Such surfaces need to be first modified with some type of adhesion agent (EP Application No. 96-303245). Organosilanes such as aminopropyltriethoxysilane (APTES) (Wu, et. Al., Chinese J. Microbiol. Immunol., 1990, 23, 147). 3-mercaptopropyltriethoxysilane (MPS) (Bhatia et. Al., Anal. Biochem. 1989, 178, 408) and glycidoxypropyltriethoxysilane (GOPS) (Maskos et. Al., Nucleic Acids Res., 1992, 20, 1679) have been used to created functionalized surfaces on glasses, silicas, optical fibers, silicon, and metal electrodes to name a few. The silanes hydrolyse onto the surface to form a robust siloxane bond with surface silanols, and also cross-link to further increase adhesion. In the case of APTES, succinnic anhydride is often used to change the amino functionality to carboxylic acid which is then attached to an amino-linked nucleic acid via carbodiimide coupling. MPS can be used to form disulfide linkages with thiol-containing biomolecules. GOPS has been used in schemes using long polyether chains to provide greater distance and flexibility between the surface and the nucleic acid probe.

Alkyl silanes have been extensively used to immobilize a wide variety of biomolecules to surfaces. The alkoxy or chloro leaving groups are particularly reactive towards hydroxyl groups found on glass, quartz, silicon and metal oxide surfaces. The surface hydroxyl group attacks the silicon in an Sn2 reaction, and the new $Si_{(surface)}$—O—$Si_{(silane)}$ bond is a siloxane-bond. Monoalkoxy or monochloro silanes can only form one siloxane bond to the surface, and therefore, the degree of surface coverage by the silane is limited by the number of available surface hydroxyl groups, which in the best of cases (glass) is no more than about 4 hydroxyls per $nm^2$. Di or tri alkoxy or chloro silanes are capable of forming more than one siloxane bond. The quantity of surface hydroxyl groups per unit area is generally too low for the silane to form more than one siloxane bond to the surface. Instead, the silanes can crosslink together to form two dimensional or multilayer networks on the surface, and therefore bridge the gap between surface hydroxyls and increase the degree of surface coverage.

This intersilane crosslinking requires a sufficient water to be present, e.g. a stoichiometric quantity of water, for the polymerization to occur, and can be carried out in the solvent used for the silanization reaction, or can be supplied by water which is adsorbed to the substrate surface. The actual mechanism of silanization depends on the conditions used. In solution, the commonly accepted mechanism is a three-step process, the first step being the hydrolysis of the chloro moieties of a silane such as octadecyltrichlorosilane (OTS) at the hydroxylic substrate surface to generate a silanetriol, which then physisorbs onto the substrate via hydrogen bonding and ultimately forms both $Si_{substrate}$—O—$Si_{silane}$ and $Si_{silane}$—O—$Si_{silane}$ cross-linking type of covalent bonds (Sagiv, J. of the Amer. Chem. Soc., 1980, 102, 92). However, it has been shown that hydrolysis of the chloro entities of OTS occurs in the bulk solution phase instead of at the substrate surface as envisaged earlier (Angst, et. al., Langmuir, 1991, 7, 2236).

The degree of surface coverage depends on several variables such as reaction time, temperature, degree of hydration of the substrates, nature of the solvent, the cleaning procedure utilized prior to silanization of substrates and the nature/morphology of the oxide layer on the substrate. Silberzan et al. (Langmuir, 1991, 7, 1647) as well as Angst and Simmons (Angst, et. al., Langmuir, 1991, 7, 2236) obtained a tightly-packed monolayer of OTS on a fully hydrated oxidized silicon wafer surface, while with a dry silicon wafer a lower surface coverage resulted. Tripp and Hair (Langmuir, 1992, 8, 1120), through an IR spectroscopic study, showed that no direct reaction occurs between OTS and either the silica surface hydroxyl groups or even the first water layer bound to the fumed silica surface. Despite the growing body of evidence concerning the importance of surface-moisture, there is not yet a standard protocol that can be used to increase reproducibility of the silane films.

Alkoxysilane 3-mercaptopropyltrimethoxysilane (MPS) has been extensively used as an immobilization agent, however, there are several problems with this reagent. Caldwell (Yee et. al., Langmuir 1991, 7, 307) showed that a silver stained MPS surface appeared rough when examined by scanning electron microscopy (SEM), and the MPS surface consisted of submicrometer size particles. They acknowledged that the MPS silane produced a multilayered structure. The group of Sligar and Bohn (Hong, et. al., Langmuir, 1994, 10, 153) found that both a 17% MPS film (diluted with n-propyltrimethoxysilane) and a 100% MPS film have similar abilities to load cytochrome $b_5$ at a 30% loading level. They performed a free-thiol assay using Ellman's reagent and discovered that the quantity of unreacted thiol groups after exposure to cytochrome $b_5$ on the surfaces is nearly identical to the quantity of unreacted thiol groups before exposure to the cytochrome. The authors concluded that most of the cytochrome was non-specifically adsorbing to the MPS film, but did not hypothesize which functionality the protein was adsorbing to. In all likelihood, the cytochrome was physisorbing to the exposed silanol-containing backbone of the disordered MPS multilayer, or to exposed patches of glass not covered by MPS. They also acknowledged that MPS produces multilayer structures, and found that the masses of MPS can be hydrolytically removed from the surface.

Alkoxy silanes are predisposed to form disordered multilayered films. This effect is compounded when the alkoxysilane contains a short alkyl chain which reduces the silane's ability to self-assemble into highly ordered films. Under unsuitable conditions of the silanization process, the alkoxysilane will tend to polymerize in solution, possibly forming large aggregates, which then migrate to the substrate surface and then polymerize onto it. Other aggregates pile up on top of each other in an uneven manner until a film many times thicker than the length of one monomer builds up. Although this coating may still be usable for immobilization purposes, it is not efficient. Much of the functionalized end of the silane is not projected normal to the substrate towards the bulk solution, but instead is oriented in every conceivable direction including parallel against the substrate surface. Clearly, this represents a severe steric barrier, and that fraction of the surface is not available for nucleic acid immobilization, although small probes such as the silver ion may be able to penetrate inside the pores. The pores may trap potential interferant molecules which may complicate biosensor data interpretation.

Trichlorosilanes are much more reactive than trialkoxysilanes, and appear to form the densest films. If the alkyl group is from 8–18 carbons in length, the self-assembly process will cause the silanes to form a "monolayer"-like coating in which the alkyl chains are packed together to nearly the same density as crystalline polyethylene. The amount of surface area (Montgomery, et. al., Anal. Chem., 1992, 64, 1170) each alkyl chain occupies is about 20 $Å^2$.

Bifunctional trichlorosilanes have been made so that other molecules can be later attached to the silanized surface. 1-Thioacetato-16-(trichlorosilyl)-hexadecane or related analogues have been described as a potential linking agent for biomolecules (Balachander, et. al., Langmuir, 1990, 6, 1621). In contrast, the short chain alkoxysilanes such as APTES, MPS, and GOPS which have been used to link nucleic acids to surfaces, usually consist of a 3-carbon tether, and tend to form disordered multilayer structures. It is possible to dilute the active silane monomer with a monomer which does not contain the linking group. For example, a simple methyl-terminated "diluent" monomer could be used to effectively "space-out" the active silane monomers that deposit on the surface.

There are many benefits that can be gained by using trichlorosilane linkers for biomolecule immobilization schemes. The avidin protein has a highly polar exterior, with many carboxylic acid and amine residues exposed. These could serve as potential binding sites for the nucleic acid probe or target molecules, or could adsorb contaminating materials such as other proteins from the solution, all of which could be detrimental to the operation of the sensor. Methyl terminated diluent silanes provide a hydrophobic alternative to polar materials which may attract unwanted contaminants. Other diluents could be used to provide other functionalities to the surface, for example, the diluent could contain alcohol groups to increase hydrophilicity, and the surface properties could be readily controlled. The number of carbons in the diluent could also be varied to control the steric environment around the active silane's functional moiety. Most importantly, the active silane could be synthesized to have a wide variety of functional groups for immobilization.

The tether group is required to supply the oligonucleotide with a reactive functionality so that it can be chemically manipulated, and to allow the oligonucleotide to extend any specified distance away from the surface (French Patent Application No. 94-12972). Thiol-tethered oligonucleotides have been immobilized onto bromoacetyl-derivatized polyacrylamide supports (U.S. Pat. No. 5,478,893).

It is desirable to be able to create both permanent and reversible linkages between the nucleic acid and the surface. One patent (U.K. Patent Application No. 89-21605) describes a phosphorus-sulfur bond placed in the backbone of an immobilized oligonucleotide which was cleaved by silver nitrate. Sulfur can also be used in a completely different way in the form of the thiol group, which can form two main types of linkages: disulfide and thioether. The reversible disulfide bond can be created using the specific reaction known as thiol-disulfide interchange, in which a thiol containing molecule reacts with a disulfide-containing molecule, so that one of the ligands from the disulfide is transferred to the original thiol group to form a new disulfide. The disulfide can be part of a bifunctional coupling agent (U.S. Pat. No. 5,399,501). The disulfide can be cleaved specifically under very mild conditions with a variety of reagents such as dithiothreitol (DTT) for example, which will regenerate the free thiol. A permanent thioether bond can be created from a thiol and a variety of reagents which contain reactive leaving groups. Thiol surfaces have been used for covalently bonding biologically active compounds (U.S. Pat. No. 4,886,755). Halobenzylic compounds readily undergo reaction with thiols, and the resulting thioether bond is very resistant to cleavage.

Solid supports carrying nucleic acids, enzymes, peptides and other biomolecules for the purposes set out herein should have a high surface density of attached groups. This is desirable so that the device can operate at maximum sensitivity in detecting and binding affinity biomolecules to be selectively bound and removed for analysis. It is also desirable to allow devices of small physical size to be prepared, for analysis of very small quantities of test reagents.

It is an object of the present invention to provide novel biochemical sensor element structures which have a very high surface density of biochemical molecules attached to the surface of a solid support.

It is a further object to provide a processes for preparation of such element structures.

SUMMARY OF THE INVENTION

The present invention provides coated supports having a very high surface density of monolayer groups attached to a substrate, and a process for preparing such supports. The monolayer groups are permanently covalently bonded to the substrate at a surface density significantly higher than any previously reported, and carry at their distal ends functional reactive groups, namely thiol groups, which can be utilized to bond either permanently or reversibly to a biomolecule such as oligonucleotide, enzyme etc., either directly or through the intermediary of a chemical tethering group or molecule. The functional, reactive thiol groups may be chemically protected until used for bonding to the tethering group or biomolecule. The invention also provides novel reagents and novel processes for preparing such coated supports, and for preparing biomolecule-presenting solid supports from the coated supports.

Thus according to an aspect of the invention, there is provided a biochemical sensor element structure comprising a solid substrate, a surface on said substrate and a monolayer of alkylsilane groups chemically bound to said surface, said alkylsilane groups being cross-linked to one another, and having distal reactive chemical groups, reactive chemical groups, the alkylsilane groups being bonded to the surface at a density of at least 14 picomoles per square centimeter of area of said surface.

The present invention also provides a process for preparing biochemical sensor element structures with very high surface density of bio-molecules chemically attached thereto. In the process, the hydroxyl group-carrying surface of the substrate is subjected to a controlled hydration process to ensure the presence thereon of an appropriate number of reactive hydroxyl groups, per unit area, for subsequent reaction with the silane. This hydration is important in achieving the very high surface density of reactive groups in the final product. Then the appropriately hydrated surface is reacted with an alkyl silane reagent in the presence of an aromatic hydrocarbon solvent of polarity and water affinity such that it removes some of the surface water. As a result, the alkylsilane bonds to the substrate surface at very high surface density, in mono-layer form, leading to the eventual formation of a biochemical sensor element structure in which there is a very high density of bio-molecules immobilized thereon, and disposed and oriented for chemical and biochemical reaction of high sensitivity.

BRIEF REFERENCE TO THE DRAWINGS

In the accompanying drawings which illustrate specific embodiments of the invention in more detail:

FIG. 4 illustrates the preparation of: A) thiol-tether to oligonucleotide, B) BMBS reagent to oligonucleotide-tether complex, and C) DNDS reagent to oligonucleotide-tether complex (Example 7 below).

FIG. 5 illustrates the immobilization of oligonucleotide-tether-linker complex to thiol functionalized surfaces by: A) permanent thioether bond formation, and B) chemoselectively reversible disulfide bond (Example 7 below).

DESCRIPTION OF THE PREFERRED EMBODIMENTS

The choice of length of the alkyl chain for the alkylsilane mono-layer is made on the basis of assuring the provision of enough exposed distal functional groups for successful bonding to the tethering molecule or biomolecule. Too short an alkyl chain on the alkylsilyl group will lead to excessive cross-linking and gelling on the substrate surface with the result that insufficient functional group is presented. Whilst alkyl chains as short as 2C can be used, it is preferred to use silane compounds with alkyl chains C8–C20, most preferable C8–C18. Preferred compounds have thiol functional terminal groups.

Specific preferred alkyl silane compounds for use in the invention are those corresponding to the general formula $Cl_3Si\text{—}(CH_2)_n\text{—}SH$ and thiol-protected derivatives thereof, where n is an integer from 2–20, preferably 8–18. Reaction of these silanes with solid substrates such as silicon, silica, chromium, chromic oxide etc., requires prior protection of the thiol group, to guard against reaction of the trichlorosilyl group with the thiol group, resulting in polymerization of the alkylsilyl reagent. Then the trichlorpsilyl group reacts with —OH of the surface (FIG. 3), and residual Si—Cl groups react together, in the presence of the surf ace water molecules, to form cross-links between adjacent groups.

A specific preferred choice of alkylsilane for forming the monolayer in structures of the present invention is 1-(thiotrifluoracetato)-11-(trichlorosilyl)-undecane (TTU), of formula:

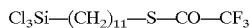

$$Cl_3Si\text{—}(CH_2)_{11}\text{—}S\text{—}CO\text{—}CF_3$$

This is a novel compound. It can be prepared by the process illustrated in accompanying FIG. 1A, and as described in more detail below, in the "Experimental" section. The use of this compound allows the formation of a very high density monolayer of exposed thiol groups (after removal of the trifluoroacetato protectant) to be placed on a variety of hydroxylic surfaces in a reproducible manner.

The use of trifluoroacetyl as the thiol protectant group, with TTU or other chosen alkyl silanes in the present invention, is particularly advantageous. It is an extremely acidic group, so that it can be removed under very mild chemical conditions, so mild that they will not otherwise interfere with the chemical structure of the surface-silane and cross-linking bonds. Substantially all of the thiolsare made available for subsequent reaction once the protectant has been removed. Moreover, F-residues, if any, are readily detectable by spectroscopic methods, to allow close monitoring of the process the trifluoroacetyl protected thiol group —S—CO—CF₃ is a specific example of a protected thiol group of general formula —S—CO—CX₃ where X is halo.

Figure 3:
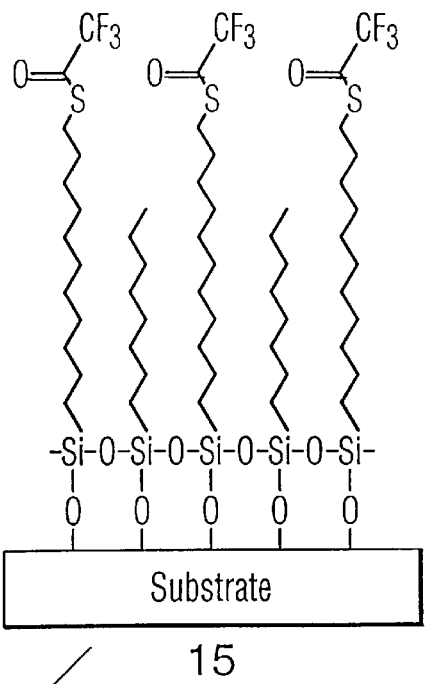
FIG. 3 illustrates: A) the silanization of the humidified substrate with a mixture of 30% TTU and 70% octyltrichlorosilane (Example 5 below), and B) the deprotection of said surface with hydroxylamine reagent (Example 6 below).
Figure 3:
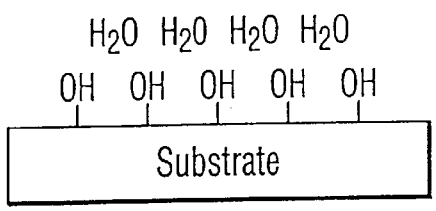
Figure 3:
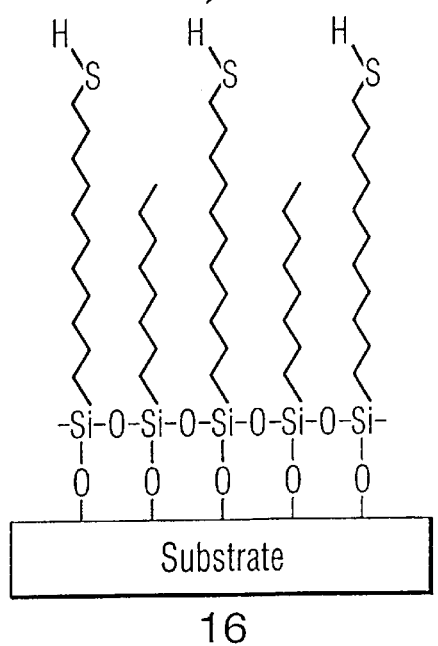

The invention in a preferred embodiment also includes the use of diluent silanes such as n-octyltrichlorosilane to further control the packing density of the thiol functionality on the surface, and to guard against excessive steric hindrance in the subsequent reactions with bio-molecules. The diluent silanes should have shorter alkyl chains than those of the terminal reactive group-carrying silanes, and the diluent silanes do not carry terminal reactive groups at their distal ends. The add further surface protection for the substrate, without significantly reducing the surface density of the functional groups. Their use and function is illustrated in FIG. 3. It is important to note that the silanization procedure later described produces monolayer films of trichlorosilanes through moisture control of the solvents and surfaces used in the preparation and is transferrable to other silanes as well. Thus an embodiment of the invention comprises a biochemical sensor element as described above and comprising at least two different alkylsilane groups bound to the surface, the first said alkylsilane group being determinated at its distal end by said functional group, and the second said alkylsilane group being a diluent silane of shorter alkyl group chain length than the first said alkylsilane group and being chemically inert at its distal end.

The process of preparing the coated supports of the present invention involves a step of reacting the prepared, cleaned substrate with the alkylsilane so that the —Si (Cl)₃ group thereon reacts with the substrate surface, e.g. Si atom, to form a linkage substrate-Si—O—Si-alkyl. This reaction requires the presence of a small amount of water on the silicon surface, and the presence of a solvent for the alkylsilane which has the correct polarity and water affinity so that it removes the appropriate amount of water from the silicon surface. The amount of surface water present should be a minimum of 42 picomoles of water per square centimeter of substrate surface, much higher than normally results from a conventional drying operation. Some of this may be contributed by water contamination of the solvent, but this contribution is normally not significant.

Suitable such solvents are aromatic hydrocarbons such as toluene, benzene, naphthalene, xylene and the like. Water miscible solvents such as dioxane are unsuitable. Highly water repellent solvents such as pentane are also unsuitable. This choice of suitable solvents based on water affinity has been described previously, for example, in the article "Role of Solvent on the Silanization of Glass with Octadecyltrichlorosilane", McGovern et al., LANGMUIR, 1994, 10, p3607–2614 (A.C.S.), the disclosure of which is incorporated herein in its entirety. The amount of water present, as substrate surface water or solvent contaminant, should not exceed 8 micromoles per 100 mls of solvent, at the time of reaction of the alkyl silane to bind to the surface, so as to avoid polymerization of the alkyl silane monomer in solution.

As noted, a preferred embodiment of the present invention is a coated substrate as described above, having the functional distal thiol end group of the alkylsilane compound bonded to the biomolecule receptor optionally and preferably through the intermediary of a tethering group. In addition to its bonding function, the tether has the function of further spacing the bio-molecule from the support, to provide greater flexibility and reduced steric interference to bonding to the bio-molecule. A wide range of chemical groups can be used as tethers, ensuring only that they are inert under conditions of bonding to the bio-molecule, and have suitable chemical functionality, preferably through end chemical groups, for chemical attachment to the thiol end group of the alkyl silane monolayer forming compound and the bio-molecule or its derivative. The tethering group or tether may be permanently bound to the alkylsilane compound, e.g. by use of dihalo-benzylic compounds such as bis(bromomethyl)benzene, conveniently used in the form of its water soluble, sulfonate derivative, as the tether. Alternatively, the tethering group may be reversibly bound to the alkylsilane compound e.g. by use of a disulfide linkage thereto, so that the support can be reconstituted for re-use following the binding of a biomolecule to the receptor thereof. An example of a compound for use as such a removable, reversible tether is a pyridyl disulfide, of formula:

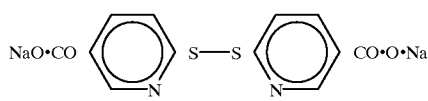

This will react with a receptor molecule such as a DNA piece to link through a reversible disulfide bond. In such cases, the bio-molecule can be removed from the complex by hydrolysis of the disulphide bond after use, and replaced with another bio-molecule for re-use of the complex. Other specific examples of suitable tethers for use in the present invention include terminally functionalized alkyl chains such as α,ω-dithio-alkanes, polyethers, phosphoramidites and modified nucleotide triphosphates, all with thiol termination.

In another embodiment, branched chain tethers are used. These have a terminal functionality such as thiol, for bonding to the thiol termination at the distal end of the alkyl silane monolayer forming compound, and a branched chain structure with functional groups such as thiol groups at the termination of one or more of the chemical branches. In such an arrangement, more than one bio-molecule may attach to each tether. This is particularly useful in circumstances where the surface of the solid support is uneven so that some of the alkyl silane chains attached thereto as a monolayer are not completely accessible for chemical reaction. A specific example of a branched chain tether is polylysine, of, say, 20–50 lysine units, providing primary amino terminal functionality to bond to the bio-molecules, or derivatives thereof carrying special terminal bonding groups for the purpose.

In a further preferred embodiment, the tether is first chemically attached to the bio-molecule and then the bio-molecule-tether complex is bound, reversibly or irreversibly, to the distal end functional group of the monolayer-forming alkylsilane. Nucleic acids can be synthesized so they contain an integral tether terminating in the thiol group. The tether in this aspect of the invention may consist of 2–20 units in length, which may be composed of either hydrocarbon alkyl chain or polyether functionalities. The tether can be a reagent in solution such as a phosphoramidite, or a modified nucleotide triphosphate which can be enzymatically attached to the nucleic acid. The tether could also be attached to the solid phase onto which the nucleic acid chain is synthesized. The thiol group of the tether reacts with either the new BMBS linking agent pyridyldisulfide-nucleic acid via DNDS reagent, which then reacts with the surface thiol provided by the silanized surface. In the case of the disulfide bond created through the latter method, cleavage of it and release of the nucleic acid can occur chemoselectively using reagents such as dithiothreitol (DTT).

Thus, according to a preferred embodiment of the invention, there is provided biochemical sensor element structure comprising: a solid support; a monolayer forming compound containing a functionality which bonds covalently to the support; a receptor bio-molecule capable of recognizing and bonding to other molecules; a tether attached to the receptor molecule and constituting a spacer group; the tether-receptor combination component of the structure being covalently attached to the functionalized monolayer forming compound.

The solid support is suitably selected from the group consisting of metals, metal oxide composites, silicas, quartz, glasses, silicon-based semiconductors, ceramics, electrophoresis membranes, filter membranes, and natural or synthetic polymers having, prior to the linkage with a spacer group, hydroxyl groups or other functional groups that can be converted into hydroxyl groups.

The element structures of the invention may be used in nucleic acid separation, purification, isolation, synthesis, amplification, diagnostic or detection applications.

In a further aspect of the invention, the receptor molecule is an enzyme, antibody, antigen or nucleic acid binding protein, instead of a nucleic acid or oligonucleotide.

In a further aspect of the invention, there is provided a method of preparing a coated support comprising: selecting a solid support; humidifying the solid support; creating on the solid support a monolayer of a compound containing a functionality which bonds to the solid support; selecting a receptor molecule capable of recognizing and bonding to other molecules; attaching a tether to the receptor molecule; using a bifunctional reagent to covalently attach the tethered receptor molecule to the functionalized monolayer compound by a chemoselectively reversible bond.

In a further aspect of the invention, the protective group is removed using aqueous hydroxylamine reagent following creation of the monolayer.

In a further aspect of the invention, the thiol group has been converted to a pyridyl disulphide group.

In a further aspect of the invention, the tether is attached to the solid support prior to use of the bifunctional reagent [i.e. solid phase oligonucleotide synthesis].

In a further aspect of the invention the tether is covalently bound to a nucleoside triphosphate and is enzymatically attached to the oligonucleotide.

In a further aspect of the invention, the bifunctional reagent contains halobenzyl functional groups.

In a further aspect of the invention, the bifunctional reagent has been rendered water soluble, e.g. by sulfonization.

In a further aspect of the invention, the bifunctional reagent is water soluble (bis(bromomethyl)benzene sulfonate, a novel compound.

In a further aspect of the invention, a reagent such as dithiothreitol is used to cleave the disulfide bond and to release nucleic acid.

The high density of alkylsilane loading on the substrate is achieved in the present invention is demonstrated by the amount of Dan surface immobilized on derivatized surfaces reported in the following examples. Table 11 below shows averages of $14.5 \times 10^{-12}$ to $54 \times 10^{-12}$ mols of DNA per square centimeter of surface area. Assuming a minimum 90% of the monolayer surface bound groups have bound to a DNA sample, this demonstrates a density of at least 14 picmoles, and at least up to about 60 picomoles, of monolayer surface bound groups per square centimeter of substrate surface.

Such high density provides additional advantages besides that of increased analytical sensitivity in practice. It also provides especially effective protection of the substrate against the deteriorative, "corrosive" effects of the aqueous medium in which the analyses using the products of the present invention are commonly used. Surface densities of alkylsilane groups, which are hydrophobic, of the high levels achieved therein, effectively seals the surface from the water. This is particularly beneficial when using metal substrates such as chromium which are subject to corrosive deterioration. Products of the present invention are thus more durable and long-lasting in practice. This sealing effect from the high density monolayer coating achieved without significant loss of sensitivity, particularly in the case where a non-terminally functionalized alkylsilane, of shorter chain length, is used in conjunction with the C8–C18 thiol-terminated alkylsilane as described above.

Other aspects of the invention will be apparent from the following detailed description of the invention.

DETAILED DESCRIPTION OF SPECIFIC PREFERRED EMBODIMENTS OF THE INVENTION

Experimental

Example 1—Synthesis of Silane

Figure 1A:
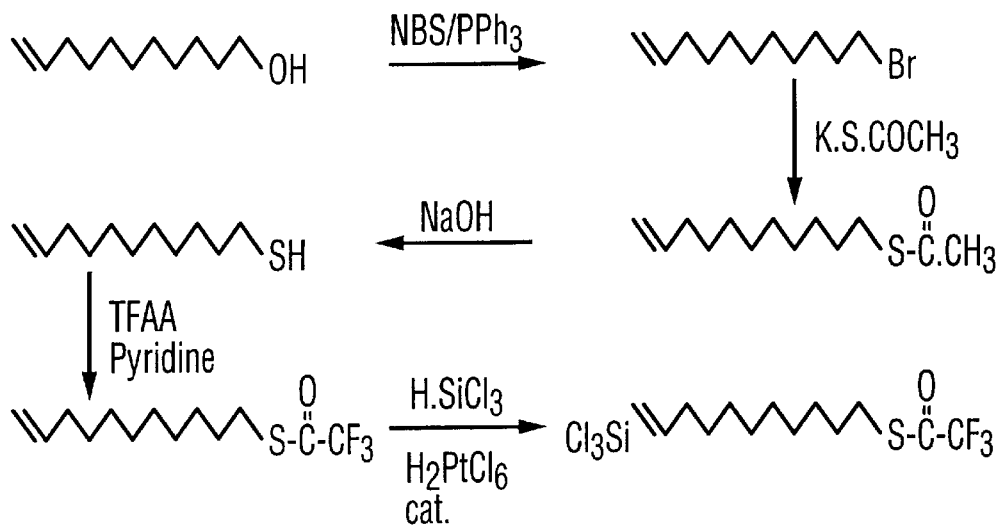
FIGS. 1A–1B depict a representation of chemical reactions leading to the generation of: A) a new silane (Example 1A below), and B) a new linker (Example 1B below).

The chemical steps in this reaction are diagrammatically illustrated in FIG. 1A appended hereto, and reagents and intermediate products are denoted by reference numerals thereon.

Materials. ω-Undecenyl alcohol 98%, potassium thioacetate 98%, trifluoroacetic anhydride 99+%, hydrogen hexachloroplatinate(IV) hydrate 99.995%, trichlorosilane 99%, neutral alumina (standard grade, 150 mesh, 58 Å), silica gel (Merck, grade 9385, 230–400 mesh 60 Å) were obtained from Aldrich and were used as received. Triphenylphosphine 98%, N-bromosuccinimide (NBS) 98%, anhydrous magnesium sulfate, phosphorus pentoxide, potassium hydroxide, hexanes, diethyl ether, tetrahydrofuran, isopropanol, methanol, and hydrochloric acid were purchased from BDH and were used without further purification. Dichloromethane and acetonitrile were purchased from BDH and were distilled over phosphorus pentoxide before use. Pyridine was obtained from BDH and was distilled over KOH before use.

Instrumentation. NMR spectra are reported in units of δ and were recorded on either a Varian Gemini 200 spectrometer using a $^1H$—$^{13}C$ switchable probe, or on a Varian VXR400S spectrometer ($^1H$, $^{13}C$, $^{19}F$, $^{29}Si$) using a 5 mm switchable probe. In the case of $^{29}Si$, either inverse-gated decoupling or DEPT were used. The samples were dissolved in $CDCl_3$ which contained 0.03% TMS. Both $^1H$ and $^{29}Si$ NMR spectra were referenced to TMS at 0.00 ppm, while $^{13}C$ NMR spectra were referenced to the center of the $CDCl_3$ triplet at 77.00 ppm.

Mass spectrometry was performed on a VG 70-250S (double focussing) mass spectrometer. The sample was subjected to electron ionization at 70 eV and an accelerating voltage of 8 KeV. The source was set at 250° C. and a pressure of $10^{-6}$ mbar. Perfluorokerosene was introduced into the spectrometer via a separate, continuous introduction system and the $CF_3^+$ ion (mass 68.9952) was used as a reference. Under these conditions, the mass spectrometer had a resolution of about 1200 (m/Δm) at 10% valley.

Elemental analysis was performed by Canadian Microanalytical Service Ltd. (Delta, B.C.). The silane was handled in an inert atmosphere during handling and analysis. All elements except oxygen were determined.

Fourier-transform infrared spectrometry was performed on Nicolet 5DXB spectrometer using the manufacturer's software. Ten scans were collected and averaged at a resolution of 2 $cm^{-1}$ and were referenced to polystyrene. The liquid samples were run neat on NaCl disks.

Synthesis of ω-Undecenyl Bromide (2). In a flame-dried dual-necked 200 ml round bottomed flask equipped with a teflon-coated magnetic stir bar and a condenser and $N_2$ inlet, were placed 8.5 g (50 mmol) of ω-undecenyl alcohol (1) and 100 ml of dry dichloromethane. The flask was covered with aluminum foil and mixture was stirred and cooled in a $CCl_4$/dry ice bath (−23° C.). 15.7 g (60 mmol) of triphenylphosphine was added to the mixture and stirred until it dissolved. 9.8 g (55 mmol) of NBS was added all at once to the mixture and was stirred at −23° C. for 1 hour. The flask was removed from the cold bath and the mixture was allowed to stir at room temperature for 30 minutes. The solution was transferred to a separatory funnel and was washed with water saturated with sodium carbonate. The organic layer was dried with $MgSO_4$, filtered, and concentrated on a rotary evaporator. The purple precipitate was extracted with 3×50 ml aliquots of hexanes using a combination of mechanical stirring, heat and sonication. The resulting suspension was filtered, and the hexanes removed on a rotary evaporator. The material was filtered through a short column of neutral alumina (5 cm height, 3 cm diameter) using hexanes under vacuum and the product was concentrated on a rotary evaporator to yield a clear liquid. Yield 10.64 g (91%); IR (neat) 3074, 2926, 1639, 1458, 999, 909 $cm^{-1}$; $^1H$ NMR (400 MHz, $CDCl_3$) δ 5.79 (1H, dddd, J=17.2, 10.2, 7.0, 7.0 Hz), 4.93 (2H, m), 3.38 (2H, t), 2.02 (2H, dd, J=6.2, 1.1 Hz), 1.83 (2H, m), 1.24–1.44 (12H, m); $^{13}C$ NMR (400 MHz, $CDCl_3$) δ 139.03, 114.05, 33.93, 33.79, 32.86, 29.38, 29.08, 28.92, 28.76, 28.18.

ω-Undecenyl Thioacetate (3). In a 50 ml round bottomed flask equipped with a teflon-coated magnetic stir bar, a condenser and $N_2$ inlet, were placed 3.50 g (15 mmol) of ω-undecenyl bromide (2), 1.71 g (15 mmol) of potassium thioacetate and 25 ml of 95% ethanol. The mixture was refluxed overnight, after which the solution was transferred to a separatory funnel, 50 ml of water was added and was extracted with 3×50 ml aliquots of hexanes. The organic layer was dried with $MgSO_4$, filtered, and concentrated on a rotary evaporator. Yield 3.32 g (97%); IR (neat) 3074, 2926, 1696, 1639, 1458, 1360, 1138, 999, 909 $cm^{-1}$; $^1H$ NMR (400 MHz, $CDCl_3$) δ 5.79 (1H, dddd, J=17.2, 10.2, 7.0, 7.0 Hz), 4.93 (2H, m), 2.85 (2H, t), 2.35 (3H, s), 2.02 (2H, dd, J=6.2, 1.1 Hz), 1.55 (2H, m), 1.24–1.44 (12H, m); $^{13}C$ NMR (400 MHz, $CDCl_3$) δ 195.91, 139.12, 114.07, 33.79, 30.62, 29.49, 29.39, 29.38, 29.14, 28.90, 28.79.

ω-Undecenyl Thiol (4). In a 50 ml round bottomed flask equipped with a teflon-coated magnetic stir bar, a condenser and $N_2$ inlet were placed 2.0 g (8.76 mmol) of ω-undecenyl thioacetate (3), 20 ml of 95% ethanol, and 5 ml of 1M NaOH. The mixture was refluxed for 1 hour, after which the solution was transferred to a separatory funnel, 50 ml of water was added and was extracted with 3×50 ml aliquots of hexanes. The organic layer was dried with $MgSO_4$, filtered, and concentrated on a rotary evaporator. Note: this material should be used immediately or stored in a frozen state. Yield 1.49 g (91%); IR (neat) 3074, 2926, 2550, 1639, 1458, 999, 909 $cm^{-1}$; $^1H$ NMR (400 MHz, $CDCl_3$) δ 5.79 (1H, dddd, J=17.2, 10.2, 7.0, 7.0 Hz), 4.93 (2H, m), 2.52 (2H, dd, 8.0, 4.0), 2.02 (2H, dd, J=6.2, 1.1 Hz), 1.57 (1H, t), 1.24–1.44 (12H, m); $^{13}C$ NMR (400 MHz, $CDCl_3$) δ 139.09, 114.07, 34.04, 33.78, 29.44, 29.39, 29.08, 29.04, 28.90, 28.36, 24.63.

ω-Undecenyl Thiotrifluoroacetate (5). In a 25 ml round bottomed flask equipped with a teflon-coated magnetic stir bar were placed 0.939 g (3.33 mmol) of ω-undecenyl thiol (4) and 5 ml of dry pyridine. 0.699 g (3.33 mmol) of trifluoroacetic anhydride was added, and the mixture was stirred at room temperature for 30 minutes while stoppered. The pyridine was removed under vacuum and the solid material was extracted with 3×20 ml aliquots of hexanes. The hexanes were removed with a rotary evaporator to yield an oil. The oil was distilled via Kugelrohr and a fraction was collected at 90° C. at 0.1 mm Hg. Yield 0.556 g (59%); IR (neat) 3074, 2926, 1704, 1639, 1458, 1285, 1203, 1162, 999, 909 $cm^{-1}$; $^1H$ NMR (400 MHz, $CDCl_3$) δ 5.79 (1H, dddd, J=17.2, 10.2, 7.0, 7.0 Hz), 4.93 (2H, m), 3.05 (2H, t), 2.02 (2H, dd, J=6.2, 1.1 Hz), 1.55 (2H, m), 1.24–1.44 (12H, m); $^{13}C$ NMR (400 MHz, $CDCl_3$) δ 184.81, 139.03, 114.11, 33.79, 29.43, 29.35, 29.32, 29.29, 28.95, 28.90, 28.67, 28.60, 24.66.

1-(Thiotrifluoroacetato)-11-(trichlorosilyl)-undecane (TTU) (6). In a flame dried heavy-walled ampoule were placed 0.99 g (3.5 mmol) of ω-undecenyl thiotrifluoroacetate (5), 0.47 g (3.5 mmol) of $HSiCl_3$, and 1 drop of a 4% soln of $H_2PtCl_6$ in isopropanol. The ampoule was sealed at −195° C. and after thawing at room temperature, it was heated at 60° C. overnight. The vial was then opened at −195° C. and the remaining $HSiCl_3$ was removed under low vacuum. The main contents of the ampoule were distilled using a Kugelrohr distillation apparatus. The product distilled at 140° C. at 0.1 mm Hg. Yield 1.17 g (80%); $^1$H NMR (400 MHz, CDCl$_3$) δ 3.05 (2H, t), 1.20–1.80 (20H, m); $^{13}$C NMR (400 MHz, CDCl$_3$) δ 184.90, 115.53, 31.82, 29.45, 29.35, 29.30, 29.00, 28.97, 28.68, 28.63, 24.32, 22.28; $^{29}$Si NMR (400 MHz, CDCl$_3$) δ 13.32; Elemental Analysis: Calcd %: C(37.47), H(5.32), F(13.68), S(7.69), Cl(25.52), Si(6.74), Found: C(38.91), H(5.58), F(8.32), S(9.05), Cl(21.92), Si(1.20).

Example 2—Single-Stranded DNA Synthesis

Materials DNA synthesis was performed on an Applied Biosystems Inc. (ABI) 392 DNA/RNA automated synthesizer, using standard CE phosphoroamidite chemistry. The reagents were purchased fresh from ABI and used as received including the benzoyl and isobutyryl-protected standard 500 mg phosphoroamidite DNA nucleotides. 0.02 M iodine oxidizing solution was used for synthesis in conjunction with 3'-thiol modification cartridges (1 μmole, 3'-Thiol modifier C3 S—S CPG, cat # 20-2933-41), both of which were purchased from Glen Research. Standard base 1 μmole synthesis columns were purchased from ABI. Concentrated ammonium hydroxide was purchased from Aldrich fresh and was refrigerated when not in use. Anhydrous acetonitrile was purchased from Aldrich and used as received. Synthesis was performed with the DMT group left on the final base, and the first two and last two trityl fractions were collected for quantitation. Poly Pak DNA purification cartridges were purchased from Glen Research. 2M Triethylamine acetate (TEAA) was purchased from ABI. Acetonitrile, trifluoroacetic acid (TFA) and ammonium hydroxide were purchased from Aldrich and used without further purification. Diluted reagents were prepared using the appropriate quantity of deionized water. p-toluene sulfonic acid, sodium acetate (ACS), sodium chloride (ACS) and acetic acid (ACS) were purchased from Aldrich.

The following DNA sequences were synthesized;

```
              5'                  4'
"control-DNA"  TAAAGCTCAAA         (SEQ ID NO:1)
"thiol-DNA"    TAAAGCTCAAA-C3-SH   (SEQ ID NO:2)
```

DNA Deprotection The standard end-synthesis program was used to cleave the product from the solid support via ammonolysis. The collection vials were sealed with teflon-coated screwcaps and were heated to 55° C. for 16 h to complete the deprotection. The vials were cooled before dividing the sample into 3 aliquots, each approximately 700 μl, in polypropylene capped mini centrifuge tubes. The ammonium hydroxide was removed on a SpeedVac set at the low temperature setting. DNA Purification A Poly-Pak solid phase purification cartridge was conditioned by pushing 2 ml of acetonitrile through the cartridge with a polypropylene syringe. The cartridge was then washed with 2 ml of 2M TEAA. The lyophilized DNA was dissolved in 1 ml of 1 M TEAA, loaded onto the cartridge, and the eluted liquid was collected and introduced again to the cartridge a total of 4 times. The cartridge was washed with 3 ml of 5% ammonium hydroxide, followed by 2 ml of water. 4 ml of 2% TFA was added to the column, followed by 2 ml of water. The product was eluted with 1 ml of 20% acetonitrile into a polypropylene vial.

Coupling Efficiency via Trityl Analysis

The collected DMT ("trityl") was diluted to 50 ml with 0.1 M p-toluene sulfonic acid (TSA) in acetonitrile. Approximately 2 ml of the diluted trityl was dispensed into a standard UV-grade quartz cuvette, and the absorbance at 498 nm was monitored, after referencing to a 0.1 M TSA blank, using a Perkin Elmer UV-vis spectrophotometer.

Quantitation of Purified DNA All of the DNA synthesis aliquots were concentrated so that 1 polypropylene tube contained the entire product of 1 synthesis column, in 1 ml of water. 20 μl of the DNA solution was added to 980 μl of PBS buffer. The sample was analysed on a Perkin Elmer UV-vis spectrophotometer at 210–310 nm, after baseline subtraction of PBS blank (10 μl water, 980 μl PBS).
Chromatographic Determination of DNA Purity A Dionex DX 500 ion-exchange chromatography system equipped with a GP40 gradient pump, and AD20 UV-vis absorbance detector, and a column switching valve (P/N 044858). The analytical column was a Dionex Nucleopac PA-100 (4×250 mm) anion-exchanger protected with a Nucleopac PA-100 guard column. The modules were controlled via the Peak Net software system. Mobile phase "A" consisted of 25 mM sodium acetate in 10% acetonitrile (pH 5.2), while mobile phase "B" consisted of 1M sodium chloride dissolved in "A". The column was equilibrated with "A" at 1.5 ml/min, and then 20 μl of the DNA sample was injected, after which the proportion of "B" increased linearly until it reached a ratio of 20% "A": 80% "B" over 40 min. "B" was increased to 100% during the next 5 minutes and the column was flushed at 1.5 ml/min for 10 minutes, then "A" was returned to 100% over 5 minutes, and the column was equilibrated for 5 minutes before the next injection. Absorbance was monitored at 260 nm.

Examples 3—Synthesis of 2,5-Bis(bromomethyl) benzenesulfonate, sodium salt (BMBS)

Figure 1B:
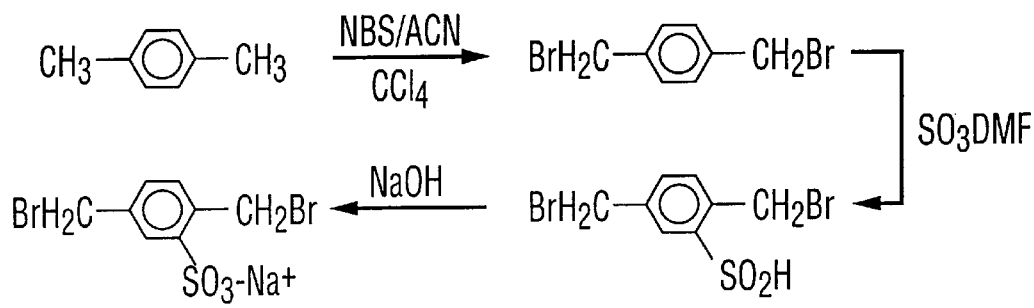

The progress and steps of this reaction are diagrammatically illustrated in appended FIG. 1B, and reagents and intermediate products designated by reference numerals thereon.

Materials. p-Xylene, carbon tetrachloride, sodium hydroxide and N-Bromosuccinimide (NBS) were obtained from BDH and used as received. 1,1'-Azobis (cyclohexanecarbonitrile) (ACN) and DMF-sulfur trioxide complex were obtained from Aldrich and used as received. DMF and benzene were obtained from BDH and were dried over 4 Å molecular sieves (Aldrich) before use.

1,4-Bis(bromomethyl)benzene (8) 19.58 g (0.11 mol) of NBS was transferred to a 250 ml round-bottomed flask containing a teflon-coated magnetic stir bar. 5.3 g (0.1 mol) of p-xylene (7) ,100 ml of carbontetrachloride and 500 mg of ACN were added to the flask and the contents were stirred and refluxed for 3 h. After cooling to room temperature, the solution was filtered and the residue was extracted with carbontetrachloride, filtered and combined with the first fraction. The solvent was removed using a rotary evaporator, and the white residue was recrystallized from heptane. Yield 23.5 g.

2,5-Bis(bromomethyl)benzenesulfonate, sodium salt (BMBS) (10) 2.64 g (0.01 mol) of 1,4-Bis(bromomethyl) benzene (8) was transferred to a 25 ml round-bottomed flask and was diluted with 7 ml of dry DMF. 1.8 g (0.012 mol) of DMF-sulfur trioxide complex was added to the flask and the mixture was stirred and heated at 100° C. for 3 h. The DMF was removed by a rotary evaporator, and the material was neutralized with 1M sodium hydroxide. The aqueous layer was extracted with benzene twice before the water was removed by azeotropic distillation with dry benzene. The material was vacuum dried overnight to yield 3.42 g of a sticky opaque substance. $^1$H NMR (400 MHz, D$_2$O) δ

7.83–7.42 (3H, m), 4.63 (4H, s); $^{13}$C NMR (400 MHz, D$_2$O) δ 132.47, 132.36, 131.99, 131.47, 61.26, 43.07, 35.39.

Example 3—Preparation of 6,6'-Dithiodinicotinic acid, disodium salt (DNDS)

1.54 g (0.005 mol) of 6,6'-Dithiodinicotinic acid (Aldrich, used as received) was stirred with 10 ml of 1M NaOH and 10 ml distilled water for 15 minutes. Most of the water was removed by rotary evaporation before the solid was azeotropically distilled with benzene and vacuum dried. Yield 1.86 g.

Example 4—Silanization Proceedure

Materials. Silicon wafers, obtained from International Wafer Service, were supplied approximately 0.4 mm thick and were polished on one side to a mirror finish. They were cut to a size of approximately 1×1 cm using a diamond-tipped pencil. Magnesium nitrate hexahydrate was obtained from Sigma. Octadecyltrichlorosilane (OTS), octyltrichlorosilane (C8), 3-mercaptopropyltrimethoxysilane (MPS) and chloroform were purchased from Aldrich. Toluene was purchased from BDH and was distilled over Na under N$_2$ immediately before use. Deionized water was obtained from an IWT (Illinois Water Treatment Company) system.

Instrumentation. X-ray photoelectron spectra were recorded on a Leybold MAX-200 X-ray Photoelectron Spectrometer using either an unmonochromated Mg K$_\alpha$ source run at 15 kV and 20 mA. The energy scale of the spectrometer was calibrated to the Ag 3d$_{5/2}$ and Cu 2p$_{3/2}$ peaks at 368.3 eV and 932.7 eV, respectively. The binding energy scale was calibrated to 285 eV for the main C(1s) feature. For all samples, a survey run (pass energy=192 eV, and from 0–1000 eV on the binding energy scale) was performed, along with higher resolution scans of the most relevant regions. Each sample was analyzed at a 90° angle relative to the electron detector using an X-ray spot size of 4×7 mm. Satellite subtraction and data normalization were performed with software obtained from the manufacturer, while quantitative and peak fitting work was performed using ESCA-Tools program. Quantitation of the low resolution spectra was performed using empirically derived sensitivity factors (obtained from the manufacturer). The sensitivity factors were C(1s)=0.34, O(1s)=0.78, Si(2p)=0.4, F(1s)=1.00.

Figure 2:
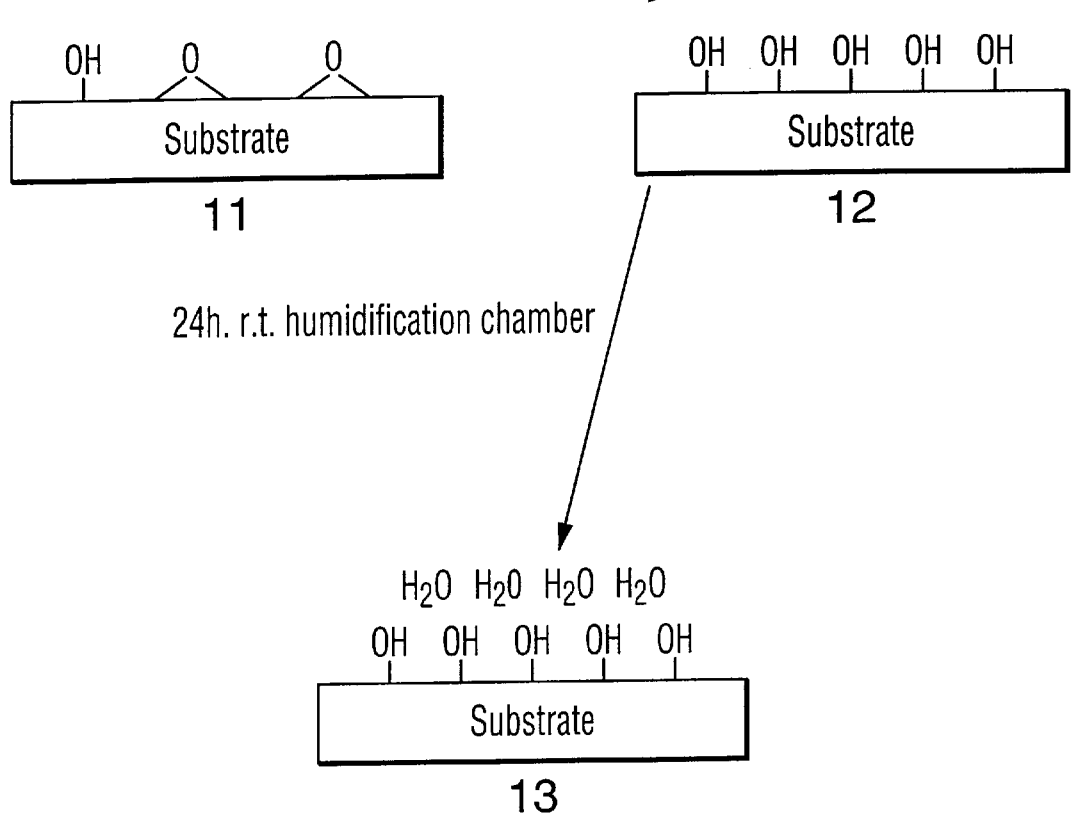
FIG. 2 illustrates the cleaning and humidification of the substrate used in silanization (Example 4 below).

Cleaning and Hydration Procedure for Silicon. This process is diagrammatically illustrated in FIG. 2 of the accompanying drawings.

The wafers 11 were first gently washed with Orvus soap solution by hand to gently remove large dust grains, then rinsed copiously with distilled water and dried in air. The wafers were then washed with ACS chloroform, blown dry with nitrogen, and then sonicated in 30% hydrogen peroxide for 30 min, to produce hydroxylated surfaces thereon, item 12. They were rinsed 5 times with deionized water, and then oven dried at 120° C. for 30 minutes. The wafers were stored in a humidity chamber which contained water saturated with Mg(NO$_2$)$_2$ overnight, to produce the desired hydroxylated, hydrated surfaces, illustrated at 13.

Example 5—Silanization of Silicon Substrates with TTU.

This process is diagrammatically illustrated in FIG. 3 part A of the accompanying drawings.

The hydrated wafers 13 were quickly removed from the humidity chambers and placed into test tubes (previously silanized with OTS) and stoppered. A dry box filled with air dried through a drierite/molecular sieve train was used to provide a low-moisture environment for the silanization reactions. The substrates were silanized for 2 hours using 2 mls of a 1×10$^{-3}$M solution in dry toluene of the mixture 30% TTU (6)/70% octyltrichlorosilane 14 to produce protected silanated substrate 15. The samples were then rinsed with dry toluene, then chloroform before being dried under nitrogen. X-ray photoelectron spectroscopic (XPS) surface analysis was performed on two 50% TTU/50 % octyltrichlorosilane coated wafers made under identical conditions and on 2 blank silicon wafers.

Silanization of Silicon Substrates with MPS. The silanization proceedure used for TTU was adopted for 3-mercaptopropyltrimethoxysilane, except that a 1×10$^{-2}$M (similar to the method of Bhatia) solution of MPS was used. X-ray photoelectron spectroscopic (XPS) surface analysis was performed on a random sample of 2 MPS coated wafers.

Example 6—Deprotection of TTU Surfaces.

This part of the process is diagrammatically illustrated in FIG. 3 part B of the accompanying drawings The TTU-coated wafers were treated with 2 ml of 0.5 M hydroxylamine in water (pH 8.5) for 2 hours at room temperature, then were rinsed with copious amounts of deionized water and finally rinsed with methanol and were blown dry with N$_2$ before storage in clean screw-capped vials, to produce substrates having deprotected thiol terminated alkylsilane groups thereon, item 16. X-ray photoelectron spectroscopic (XPS) surface analysis was performed on two deprotected 50% TTU/50% octyltrichlorosilane coated wafers.

Example 7—Radiolabelling Experiments

Day 1 500 ml of PBS buffer (pH 7.5) was made from tablets (Sigma) dissolved in deionized water (Millipore). 100 ml of this buffer was transferred to a separate container called "label buffer" and MgSO$_4$ (BDH ACS grade, heated to 150° C. for 30 minutes prior to use) was added to the solution to a concentration of 10 mM. The two solutions were autoclaved at 120° C. for 30 minutes.

The contents of 3 tubes of "thiol DNA" were dissolved in a total of 200 µl of label buffer and combined into one eppindorf tube. The same was done for "control DNA".

2 µl of the thiol DNA was added to 500 µl of water and its U.V. absorbance was measured using a Beckman DU640 spectrophotometer. $\lambda_{260nm}$=0.1069, $\lambda_{280nm}$=0.0593

2 µl of the control DNA was added to 500 µl of water and its U.V. absorbance was measured. $\lambda_{260nm}$=0.8393, $\lambda_{280nm}$=0.7273

One container of Polynucleotide Kinase (Pharmacia, cat # 27-0736-01, 200 u, obtained recently and stored at −20° C. unopened before use) was diluted with 20 µl of PBS, and was stored on the benchtop in a cooler at −20° C. when not in immediate use.

Two containers of γ$^{32}$P ATP (Amersham, special order, contains no β-mercaptoethanol (BME) or other preservatives, dissolved in 50% ethanol) had arrived a few hours earlier, and were made to each have an activity of 2 mCi/ml in a total volume of 125 µl for the previous day.

Note: all experiments involving the handling of radiochemicals were done behind lcm thick plexiglas shields in a specially designated area of the lab. Tongs or a small plexiglas eppindorf tube holder were used to manipulate the sample tubes whenever possible and safetyglasses were worn.

198 µl of "thiol DNA" solution and 9 µl of kinase solution and 125 µl of ATP solution were mixed together.

25 µl of control DNA solution and 173 µl of label buffer and 9 µl of kinase solution and 125 µl of ATP solution were mixed together.

Both tubes were incubated at 37° C. in a circulating water bath overnight (16 h).

Day 2 100 ml of PBS solution was adjusted to a pH of 3 and was autoclaved at 120° C. for 30 minutes.

Both DNA samples were extracted twice with 200 μl of chloroform (BDH spectrograde), and 75 μl of the aqueous phase was removed with care taken not to include material at the interface. 5 μl of the solutions were stored in the −20° C. freezer.

70 μl of "thiol DNA" was reacted with approximately 5 mg of DNDS (21) for 1 h at room temperature—FIG. 4C.

Another aliquot of 70 μl of "thiol DNA" was reacted with approximately 5 mg of BMBS (10) for 1 h at room temperature—FIG. 4B.

70 μl of "control DNA" was allowed to sit for 1 h at room temperature.

2 NAP-5 desalting columns (Pharmacia) were equilibrated with PBS (pH 7.5) buffer according to the manufacturer's instructions, while a separate NAP-5 column was equilibrated with PBS (pH 3).

The "control DNA" and DNDS-reacted sample were loaded onto the NAP-5 columns which were previously equilibrated with PBS (pH 7.5), after which 430 μl of PBS (pH 7.5) was added and the liquid was allowed to percolate onto the column. BMBS-reacted sample was loaded onto the separate NAP-5 column (pH 3), 430 μl of PBS (pH 3) was added and the liquid was allowed to percolate onto the column.

900 μl of the appropriate buffer was used to elute the samples, which were collected in 1 ml eppindorfs.

10 μl of 1M NaOH was added to the BMBS sample to neutralize the acid.

A 100 μl aliquot was removed from each sample and stored at −20° C.

A special cell was previously constructed (Machine Shop, Dept of Chemistry, University of Toronto) to house the silanized surfaces. It was fabricated from stainless steel and consisted of two 1 cm thick slabs which could be secured together with nine bolts. In the top slab, 12 holes were drilled through, each 5 mm diameter, each spaced approximately 1.5 cm away from its nearest neighbour or an edge. A silicone gasket was cut so that 12 (5 mm diameter) holes lined up with the top slab. 6 deprotected 30% TTU wafers were positioned over the holes on one side of the silicone gasket, and 6 100% MPS wafers were positioned on the other side so that the polished side of the wafers were facing toward the holes. Care was taken to ensure that the wafers were centered over the holes and that no leakage could occur. A rubber gasket was placed over the backside of the wafers, and the bottom slab was positioned on top. The entire assembly was flipped over so that the holes were now visible, and the bolts were fastened so that a snug, but not overly tight fit was achieved.

200 μl of the samples which eluted from the NAP-5 columns were added to the samples in the following pattern;

| Sample | TTU surfaces | | MPS surfaces | |
| --- | --- | --- | --- | --- |
| control-DNA | #1 | #2 | #1 | #2 |
| DNDS-treated thiol-DNA | #1 | #2 | #1 | #2 |
| BMBS-treated thiol-DNA | #1 | #2 | #1 | #2 |

The samples were allowed to react with the surfaces overnight (16 h)—FIGS. 5A and 5B.

Day 3 The liquids were removed from the cell, and the surfaces were washed in situ with 2×200 μl of PBS (pH 7.5) and then 2×200 μl of distilled water. Care was taken to remove all the liquid before the cell was opened. The samples were removed, and it was apparent that no leakage took place. The wafers were placed shiny side up in 20 ml vials, filled with 20 ml of distilled water and and swirled at room temperature for one hour. The water was replaced and the process repeated twice more. 1 ml of the final washing from one randomly chosen sample (TTU DNDS #2) was saved.

The wafers were each placed in separate 20 ml plastic scintillation vials (Fisher 3-337-11B) which were filled with 20 ml of ACS aqueous scintillant (Amersham NACS104). 1 ml of the final washing from (TTU DNDS #2) was put into a 20 ml plastic scintillation vial and 19 ml of scintillant was added. The samples were counted using a Beckman LS 5000TD automated counter using the standard $^{32}P$ program.

Day 4 30 μl aliquots of the material which eluted from the NAP-5 columns the previous day were added to separate 20 ml scintillation vials and diluted with 20 ml of scintillant fluid. Three scintillation vials were filled with scintillant fluid to be used as blanks. These samples were counted one day after the surfaces were counted, plus or minus 1 hour.

50 μl of the material which eluted from the NAP-5 columns were each diluted with 500 μl of millipore water, and their U.V. absorbance at 260 nm was measured using a Beckman DU640 spectrophotometer.

Results and Discussion

TTU (6) was found to be a very practical material for monolayer immobilization of nucleic acids onto hydroxylic surfaces for many reasons.

The TTU silane monolayer films were characterized by angle-resolved XPS (ARXPS) which determined the thickness of 50% TTU/50% octyltrichlorosilane film on silicon substrate before deprotection (see FIG. 3, structure 15). Tables 2 and 3 show both the experimental results and a comparison with a 3-layer theoretical model (Andrade, Surface and Interfacial Aspects of Biomedical Polymers, Vol. 1, 1985) which provides values for the film thickness of the hydrocarbon portion of the film (tb), the thickness of the fluorinated portion (tc), and degree of coverage relating to the fluorinated portion (fc). In order to produce the theoretical modeled values, the mean free path (MFP) λ values of each determined value were estimated to be $Si(2p)\lambda a=28$, $C(1s)\lambda b=35$, and $F(1s)\lambda c=44$ (Andrade). The thickness of the hydrocarbon portion of the film was found to be 15 Å, and the thickness of the fluorinated portion was found to be 1 Å in both samples. The degree of coverage was found to be 0.91 and 0.89, which averages to 0.90. From molecular models, the entire length of the TTU molecule was measured at 17.15 Å, and the length of octyltrichlorosilane was measured at 8.85 Å, therefore, the average thickness of the 50% TTU/50% octyltrichlorosilane film was 13 Å. It is clear that the experimentally determined overall film thickness of the silane is 15 Å+1 Å=16Å, which compares well to the ideal value of 13 Å, considering that the accuracy of this technique is about ±2 Å. Since the degree of coverage is 90%, the silane film is very close to the ideal monolayer.

The ARXPS results of the TTU silanization system were compared to a commonly used thiol-containing silane, 3-mercaptopropyltrimethoxysilane (MPS). Using a two-layer theoretical model for comparison, it was found that 100% MPS films had an average thickness of 33.5 Å and average surface coverage of roughly 0.66. From computer models, the hydrocarbon chain of MPS is only 2.86 Å. Therefore, the MPS film is the equivalent of 11 monolayers in thickness. The low coverage value of 66% indicates the MPS film is very porous.

By virtue of its trifluoroacetyl-protected thiol group, the immobilized silane can be characterized by X-Ray photoelectron spectroscopy (XPS) before and after deprotection (FIG. 3, 15–16). Table 1 shows a comparison of 50%

TTU/50% octyltrichlorosilane film on silicon substrate before and after deprotection. It is readily apparent that 89.2% of the protected thiol groups were effectively deprotected by the hydroxylamine reagent (0.5M, pH 7.5). This reagent and the conditions used were found to be optimal for deprotecting TTU silane films.

The oligonucleotide sequences "control-DNA" and "thiol-DNA" were chosen as representative oligonucleotide probes. Analysis of the DMT cation by U.V.-visible spectroscopy at 498 nm showed the stepwise yields for both types of DNA were above 97%, and ion-exchange HPLC revealed the purified products to be sufficiently pure (about 90%) for immobilization use.

$^{32}P$ radiolabelling was used to determine the quantity of immobilized oligonucleotides onto the silane wafer. Several key factors were incorporated into the experimental design. "Control-DNA" was used to evaluate the amount of DNA "immobilized" by non-specific adsorption. Since "control-DNA" does not contain any disulfide or thioether-forming functional groups, it can only stick to the silane surfaces through non-covalent physisorption forces such as hydrogen bonding and hydrophobic-hydrophobic interactions. "Thiol-DNA" contains a primary thiol group attached to a short hydrocarbon tether which can react with BMBS or DNDS which will then subsequently react with the thiol groups on the silanized surfaces through covalent forces. Before radiolabeling the oligonucleotides, the quantity of both types of nucleotides were checked by U.V. absorption, and their concentrations were adjusted so that both were similar. Both 30% TTU/70% octyltrichlorosilane and 100% MPS surfaces were compared for immobilization yield using the three types of $^{32}P$-labeled DNA generated (control-DNA, DNDS-DNA, and BMBS-DNA) from the same batch. In this way, both the MPS and the TTU surfaces were treated with the same concentration and radioactivity of labeled DNA products at the same time. The cell used for immobilization ensured that each surface had 0.196 cm$^2$ of surface area exposed for immobilization, therefore the data collected on all surfaces are comparable.

The raw data showing the background number of counts per minute (CPM) is shown in Table 6, and the raw CPM on each wafer is shown in Table 7, with and without background subtraction. The measured concentrations of radiolabelled products in solution are shown in Table 8, the measured CPM/unit volume is shown in Table 9 (with and without time correction), and the calculated CPM/mol DNA is shown in Table 10. The time correction used in Table 9 was necessary since the CPM measurement in solution was performed one day after the CPM from the surfaces was determined, and it was calculated using the formula $N_{(t)}=N_{(0)}e^{-(\lambda t)}$ where $\lambda$ is the decay constant for $^{32}P$ (0.0447 d$^{-1}$) and the time was one day.

The final results are tabulated in Table 11, and the general structures of the modified and immobilized nucleic acids are shown in FIGS. 4 and 5. It is very clear that the TTU silanized surface can load very high levels of BMBS-oligonucleotides (see FIG. 4, compound 20; and FIG. 5, structure 23) compared to MPS surfaces. In particular, BMBS-DNA was measured at an average of 54.00 pmol/cm$^2$ on the TTU surfaces, whereas only 13.78 pmol/cm$^2$ was found on average on the MPS surfaces, an increase of 392%. This is a significant gain considering that the MPS film was found to exist as a very thick multilayer (11 monolayer units) using ARXPS discussed earlier compared to the TTU monolayer. The two systems loaded approximately the same levels of DNDS-DNA (FIG. 4, 22; and FIG. 5, 24) although the exact reason is unclear. It is apparent that TTU surfaces do not attract as much non-specific adsorption as MPS surfaces (ratio 1:3 of control-DNA) and it is clear that the results from the DNDS-DNA and BMBS-DNA immobilized TTU surfaces are significantly different from the control-DNA sample. The same level of confidence cannot be said of the MPS system, and it is possible that some of the CPM measured on MPS surfaces is due to non-specific adsorption effects. Although it is possible that some non-specific adsorption could be present on DNDS-DNA and BMBS-DNA on TTU surfaces, it is generally believed that as the quantity of immobilized molecules increases, the quantity of non-specific adsorption decreases because the number of available binding sites decreases. The TTU results for DNDS-DNA and BMBS-DNA show improved reproducibility when compared to the MPS results ±11.55% and ±7.24% vs ±21.34% and ±38.53%).

The immobilized BMBS-DNA on TTU surfaces results can be compared to the avidin-biotin immobilization system. Using a thin layer of avidin on a gold surface and subsequent immobilization of $^{32}P$ radiolabelled biotinylated DNA (to be published), it was found that 0.973 pmol/cm$^2$ of DNA was immobilized. The TTU surfaces therefore immobilize 5550% nucleic acid compared to avidin-biotin method. The reason is that avidin is a large protein (approximately 100 Å in diameter) with only 4 biotin binding sites. Most of the avidin-coated surface is therefore wasted space, while the TTU silane self-assembles to provide the maximum density of functional groups per unit area with a theoretical spacing of the diameter of one hydrocarbon chain.

The methodology is applicable to silanes and substrates other than TTU (6) and silicon wafers. For example, the hydrocarbon chain length can be shortened or extended from C2 to C20 in both the protected thiol-containing silane, as well as the silane used for dilution purposes. The diluting silane can terminate in a methyl group as does octyltrichlorosilane, or it could terminate in a wide variety of functionalities such as alcohol, amine, ammonium, carboxylic or sulfonic acid to provide the silane film with a range of chemical functionalities. The silanization system discussed can be applied to a wide range of substrates which are hydroxyl-bearing in nature; for example, silicas such as oxidized silicon, quartz, and glasses, ceramics, metal oxide surfaces such as aluminum, chromium, steels, tin oxide, palladium and platinum to name a few. The hydration protocol described is also applicable to these surfaces as well.

The new linker BMBS (10) is also useful for immobilizing oligonucleotides to substrates without attachment through any silane. The benzylbromide functionality of BMBS will react with a wide variety of nucleophiles on functionalized polymers such as polystyrene/divinyl benzene, polyacrylamide, carbohydrate polymers such as celluloses, dextroses, sepharoses, modified polyethylene, and polytetrafluoroethylene. BMBS can be used as a homobifunctional reagent for the attachment of many types of biomolecules in general to other biomolecules such as proteins, antibodies and oligonucleotides, and for attachment of biomolecules to many types of substrates as discussed earlier.

The thiol containing tether attached to the solid phase olignucleotide synthesis column is commercially available, however other types of thiol tethers could be used for this purpose. The tether can consist of 2–50 units in length, which may be composed of either hydrocarbon or polyether functionality. The tether need not be an integral part of the solid phase oligonucleotide synthesis column, but can also be a reagent used in solution such as a phosphoramidite, or a modified nucleotide triphosphate which can be enzymatically attached to the nucleic acid. The prepared reagent DNDS (21) can be used to convert the thiol-tethered oligonucleotide to a reactive disulfide-forming oligonucleotide, or could be used to convert other biomolecules to their pyridyldisulfides for use in biomolecule conjugation reactions, or for immobilization purposes.

TABLE 1

Angle-Resolved XPS of 50% TTU, 50% C8 on Silicon, (Protected)
3-Layer Model, Sample #1

| Take-Off Angle (θ) | XPS Elements | Exp. Ratio | Fit Ratio |
|---|---|---|---|
| 20 | F1s/C1s | 0.103 | 0.109 |
|    | C1s/Si2p | 2.617 | 2.734 |
|    | F1s/Si2p | 0.269 | 0.299 |
| 30 | F1s/C1s | 0.117 | 0.092 |
|    | C1s/Si2p | 1.858 | 1.641 |
|    | F1s/Si2p | 0.217 | 0.151 |
| 45 | F1s/C1s | 0.122 | 0.082 |
|    | C1s/Si2p | 1.261 | 1.058 |
|    | F1s/Si2p | 0.154 | 0.087 |
| 90 | F1s/C1s | 0.156 | 0.075 |
|    | C1s/Si2p | 0.708 | 0.699 |
|    | F1s/Si2p | 0.110 | 0.053 |

Variables: $\lambda a = 28$, $\lambda b = 35$, $\lambda c = 44$, $tb = 15$Å, $tc = 1$Å, $fc = 0.91$

TABLE 2

Angle-Resolved XPS of 50% TTU, 50% C8 on Silicon, (Protected)
3-Layer Model, Sample #2

| Take-Off Angle (θ) | XPS Elements | Exp. Ratio | Fit Ratio |
|---|---|---|---|
| 20 | F1s/C1s | 0.098 | 0.107 |
|    | C1s/Si2p | 2.663 | 2.660 |
|    | F1s/Si2p | 0.262 | 0.284 |
| 30 | F1s/C1s | 0.097 | 0.090 |
|    | C1s/Si2p | 1.972 | 1.629 |
|    | F1s/Si2p | 0.191 | 0.146 |
| 45 | F1s/C1s | 0.081 | 0.080 |
|    | C1s/Si2p | 1.342 | 1.062 |
|    | F1s/Si2p | 0.109 | 0.085 |
| 90 | F1s/C1s | 0.104 | 0.074 |
|    | C1s/Si2p | 0.828 | 0.706 |
|    | F1s/Si2p | 0.086 | 0.052 |

Variables: $\lambda a = 28$, $\lambda b = 35$, $\lambda c = 44$, $tb = 15$Å, $tc = 1$Å, $fc = 0.89$

TABLE 3

Angle-Resolved XPS of 100% MPS on Silicon, 2-Layer Model, Sample #1

| Take-Off Angle (θ) | XPS Elements | Exp. Ratio | Fit Ratio |
|---|---|---|---|
| 20 | C1s/Si2p | 2.75 | 2.053 |
| 30 | C1s/Si2p | 1.93 | 1.675 |
| 45 | C1s/Si2p | 1.33 | 1.266 |
| 90 | C1s/Si2p | 0.90 | 0.902 |

Variables: $\lambda a = 28$, $\lambda b = 35$, $ta = 33$Å, $fa = 0.65$

TABLE 4

Angle-Resolved XPS of 100% MPS on Silicon, 2-Layer Model, Sample #2

| Take-Off Angle (θ) | XPS Elements | Exp. Ratio | Fit Ratio |
|---|---|---|---|
| 20 | C1s/Si2p | 2.60 | 2.164 |
| 30 | C1s/Si2p | 2.03 | 1.770 |
| 45 | C1s/Si2p | 1.19 | 1.344 |
| 90 | C1s/Si2p | 0.85 | 0.957 |

Variables: $\lambda a = 28$, $\lambda b = 35$, $ta = 34$Å, $fa = 0.66$

TABLE 5

XPS of 50% TTU Surfaces on Silicon, Before and After $NH_2OH$ Deprotection

| Sample Description | XPS Elements | Exp. Ratio | Rel. Error % | deprotect / Protect |
|---|---|---|---|---|
| Blank Silicon | | | | |
| A) Blank #1 | F1s/C1s | 0.00 | | |
| Blank #2 | F1s/C1s | 0.00 | | |
| Before Deprotection | | | | |
| B) 50% TTU surface #1 | F1s/C1s | 0.140 | | |
| 50% TTU surface #2 | F1s/C1s | 0.100 | | |
| average | F1s/C1s | 0.120 | ± 16.7% | |
| After Deprotection | | | | |
| C) 50% TTU surface #1 | F1s/C1s | 0.015 | | |
| 50% TTU surface #2 | F1s/C1s | 0.012 | | |
| average | F1s/C1s | 0.013 | ± 7.7% | |

$$\frac{0.013}{0.120} \times 100\% = 89.2\%$$

TABLE 6

CPM Background

| Sample | CPM | 2sig |
|---|---|---|
| blank 1 | 11.00 | ±6.63 |
| blank 2 | 12.00 | ±6.93 |
| blank 3 | 17.00 | ±8.25 |
| blank$_{avg}$ | 13.33 | ±12.65 |

TABLE 7

Surface-Immobilized DNA CPM with and without Background Subtraction

| Sample | Raw CPM | Background Subtracted | Rel. Error % |
|---|---|---|---|
| TTU control 1 | 1122 ± 67 | 1109 ± 68 | ±6.15% |
| TTU control 2 | 755 ± 55 | 742 ± 5 | ±7.60% |
| TTU DNDS 1 | 4237 ± 130 | 4224 ± 131 | ±3.09% |
| TTU DNDS 2 | 3358 ± 116 | 3345 ± 117 | ±3.48% |
| TTU BMBS 1 | 7725 ± 176 | 7549 ± 177 | ±2.34% |
| TTU BMBS 2 | 6546 ± 162 | 6533 ± 162 | ±2.48% |
| MPS control 1 | 2496 ± 100 | 2483 ± 101 | ±4.05% |
| MPS control 2 | 3281 ± 115 | 3268 ± 115 | ±3.53% |
| MPS DNDS 1 | 3204 ± 113 | 3191 ± 114 | ±3.57% |
| MPS DNDS 2 | 4932 ± 141 | 4919 ± 141 | ±2.87% |
| MPS BMBS 1 | 1117 ± 67 | 1104 ± 68 | ±6.16% |
| MPS BMBS 2 | 2501 ± 100 | 2488 ± 101 | ±4.05% |

TABLE 8

Concentration of Radiolabelled DNA for Immobilization

| Sample | $Abs_{260\ nm}$ | pathlength | molar absorptivity | concentration |
|---|---|---|---|---|
| control | 0.1063 | 0.2 cm | 136300 $cm^{-1} \times mol^{-1} \times l$ | $4.29 \times 10^{-11}$ mol/$\mu l$ |
| DNDS | 0.0852 | 0.2 cm | 136300 $cm^{-1} \times mol^{-1} \times l$ | $3.44 \times 10^{-11}$ mol/$\mu l$ |
| BMBS | 0.0958 | 0.2 cm | 136300 $cm^{-1} \times mol^{-1} \times l$ | $3.87 \times 10^{-11}$ mol/$\mu l$ |

TABLE 9

Scintillation of Radiolabelled DNA Derivatives in Solution with Time Correction

| Sample | CPM (June 20)/30 $\mu l$ | CPM (June 20)/$\mu l$ | Rel. Error % | CPM (June 19)/$\mu l$ |
|---|---|---|---|---|
| control | 2646540 ± 14556 | 88218 ± 486 | ±1.55% | 92276 ± 1.55% |
| DNDS | 1310340 ± 10221 | 43678 ± 341 | ±1.78% | 45687 ± 1.78% |
| BMBS | 737400 ± 7669 | 24580 ± 256 | ±2.04% | 25711 ± 2.04% |

TABLE 10

Radioactivity/mol DNA

| Sample | CPM/mol |
|---|---|
| control | $2.15 \times 10^{15}$ cpm/mol DNA ± 2.45% |
| DNDS | $1.33 \times 10^{15}$ cpm/mol DNA ± 2.95% |
| BMBS | $0.665 \times 10^{15}$ cpm/mol DNA ± 3.08% |

TABLE 11

Surface Immobilization of DNA on TTU and MPS Surfaces

| Sample | mol DNA | Mol DNA/cm2 | avg_mol/cm2 | sample_var. | ratio |
|---|---|---|---|---|---|
| TTU control 1 | $0.515 \times 10^{-12}$ ± 8.60% | $2.63 \times 10^{-12}$ ± 8.60% | $2.19 \times 10^{-12}$ | ±20.1% | 1 |
| TTU control 2 | $0.344 \times 10^{-12}$ ± 10.05% | $1.75 \times 10^{-12}$ ± 11.05% | | | |
| TTU DNDS 1 | $3.18 \times 10^{-12}$ ± 6.04% | $16.2 \times 10^{-12}$ ± 7.04% | $14.5 \times 10^{-12}$ | ±11.6% | 6.6 |
| TTU DNDS 2 | $2.52 \times 10^{-12}$ ± 6.43% | $12.9 \times 10^{-12}$ ± 7.43% | | | |
| TTU BMBS 1 | $11.4 \times 10^{-12}$ ± 5.42% | $57.9 \times 10^{-12}$ ± 6.42% | $54.0 \times 10^{-12}$ | ±7.2% | 24.7 |
| TTU BMBS 2 | $9.82 \times 10^{-12}$ ± 5.56% | $50.1 \times 10^{-12}$ ± 6.56% | | | |
| MPS control 1 | $1.15 \times 10^{-12}$ ± 6.50% | $5.87 \times 10^{-12}$ ± 7.50% | $6.82 \times 10^{-12}$ | ±13.8% | 3.1 |
| MPS control 2 | $1.52 \times 10^{-12}$ ± 5.98% | $7.76 \times 10^{-12}$ ± 6.98% | | | |
| MPS DNDS 1 | $2.40 \times 10^{-12}$ ± 6.52% | $12.2 \times 10^{-12}$ ± 7.52% | $15.6 \times 10^{-12}$ | ±21.3% | 7.1 |
| MPS DNDS 2 | $3.70 \times 10^{-12}$ ± 5.82% | $18.9 \times 10^{-12}$ ± 6.82% | | | |
| MPS DNDS 1 | $1.66 \times 10^{-12}$ ± 9.24% | $8.47 \times 10^{-12}$ ± 10.24% | $13.8 \times 10^{-12}$ | ±38.5% | 6.3 |
| MPS DNDS 2 | $3.74 \times 10^{-12}$ ± 7.13% | $19.1 \times 10^{-12}$ ± 6.82% | | | |

What is claimed is:

1. A biochemical sensor element structure comprising a solid substrate, a surface on said substrate and a monolayer of alkylsilane groups chemically bound to said surface, said alkylsilane groups being cross-linked to one another, and having distal reactive chemical groups, the alkylsilane groups being bonded to the surface at a density of at least 14 picomoles per square centimeter of area of said surface, the distal chemical reactive groups comprising protected thiol groups of general formula —S—CO—$CX_3$, wherein X is halo, and being adapted for deprotection and chemical bonding directly or indirectly to a bio-molecule.

2. The biochemical sensor element structure of claim 1 wherein the alkylsilane groups have from 2–20 carbon atoms in the alkyl chain.

3. The biochemical sensor element structure of claim 2 wherein the alkylsilane groups have from 8–18 carbon atoms in the alkyl chain.

4. The biochemical sensor element structure of claim 3 wherein X is fluorine.

5. The biochemical sensor element structure of claim 3 wherein the substrate is silicon, metal, silicon oxide or metal oxide.

6. The biochemical sensor element structure of claim 5 wherein the alkylsilane groups are bonded to the substrate surface through Si—O— groups, and are cross-linked to one another through the same Si-atoms.

7. The biochemical sensor element structure of claim 6 wherein the alkylsilane group has a linear alkyl chain of 11 methylene groups.

8. The biochemical sensor element structure of claim 7 wherein the alkylsilane group is derived from 1-(thiofluorocetato)-11-trichlorosilyl)undecane.

9. The biochemical sensor element structure of claim 1 comprising at least two different alkylsilane groups bound to the surface, the first said alkylsilane group being terminated at its distal end by said functional group, and a second said alkyl silane group being a diluent silane of shorter alkyl group chain length than the first said alkylsilane group and being chemically inert at its distal end.

* * * * *

```
                        SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: yes (iv) ANTI-SENSE: no (v) FRAGMENT TYPE: internal
```

```
            (vi) ORIGINAL SOURCE:

(vii) IMMEDIATE SOURCE: synthetic (xi) SEQUENCE DESCRIPTION: SEQ ID NO: 1:

TAAAGCTCAA A                                                                11

(2) INFORMATION FOR SEQ ID NO: 2:

(i) SEQUENCE CHARACTERISTICS:
                 (A) LENGTH: 11 base pairs
                 (B) TYPE: nucleic acid
                 (C) STRANDEDNESS: single
                 (D) TOPOLOGY: linear (ii) MOLECULE TYPE: other nucleic acid (iii) HYPOTHETICAL: yes (iv) ANTI-SENSE: no (vi) ORIGINAL SOURCE:

(vii) IMMEDIATE SOURCE: synthetic (ix) FEATURE:
                 (A) NAME/KEY: thiol-DNA
                 (B) LOCATION: nucleotide 11 in sequence
                 (C) IDENTIFICATION METHOD:
                 (D) OTHER INFORMATION: C3 of the adenine at
                     position 11 has been modified by the
                     addition of a thiol group (xi) SEQUENCE DESCRIPTION: SEQ ID NO: 2:

TAAAGCTCAA N                                                                11
```